(12) United States Patent
Goldberg et al.

(10) Patent No.: US 7,294,309 B1
(45) Date of Patent: Nov. 13, 2007

(54) SMALL VOLUME LIQUID HANDLING APPARATUS AND METHOD

(75) Inventors: Jeffrey B. Goldberg, San Diego, CA (US); William Spencer, Carlsbad, CA (US); Bruce K. Bridges, Cardiff, CA (US)

(73) Assignee: Takeda San Diego, Inc., San Diego, CA (US)

( * ) Notice: Subject to any disclaimer, the term of this patent is extended or adjusted under 35 U.S.C. 154(b) by 476 days.

(21) Appl. No.: 10/438,789

(22) Filed: May 15, 2003

(51) Int. Cl.
*B01L 3/02* (2006.01)
(52) U.S. Cl. .................. 422/100; 422/99; 422/102; 73/863.01; 436/180; 222/195
(58) Field of Classification Search .......... 422/99–102; 436/180; 222/630, 195; 73/863.1
See application file for complete search history.

(56) References Cited

U.S. PATENT DOCUMENTS

| | | | |
|---|---|---|---|
| 5,403,617 A * | 4/1995 | Haaland .................. 427/421.1 |
| 5,558,837 A * | 9/1996 | Tsukishima .................. 422/99 |
| 5,738,728 A * | 4/1998 | Tisone .......................... 118/638 |
| 5,741,554 A | 4/1998 | Tisone |
| 5,916,524 A | 6/1999 | Tisone |
| 6,063,339 A | 5/2000 | Tisone et al. |
| 6,446,878 B1 * | 9/2002 | Chandra et al. ................ 239/1 |
| 6,737,022 B1 * | 5/2004 | Sutton et al. .................. 422/70 |
| 2002/0064482 A1 * | 5/2002 | Tisone et al. ............... 422/100 |
| 2002/0092366 A1 * | 7/2002 | Brock et al. ............. 73/863.32 |

\* cited by examiner

*Primary Examiner*—Jill Warden
*Assistant Examiner*—Jyoti Nagpaul
(74) *Attorney, Agent, or Firm*—David J. Weitz

(57) ABSTRACT

A fluid dispensing system comprising: a fluid container; a dispensing head in fluid communication with the fluid container; a displacement mechanism which delivers fluid from the fluid container to the dispensing head such that an aliquot of liquid is delivered to a distal end of the dispensing head where the aliquot of liquid is retained; and a pressurized gas displacement mechanism which delivers an aliquot of gas to the distal end of the dispensing head which causes the aliquot of liquid retained at the distal end of the dispensing head to separate from the distal end of the dispensing head.

32 Claims, 29 Drawing Sheets

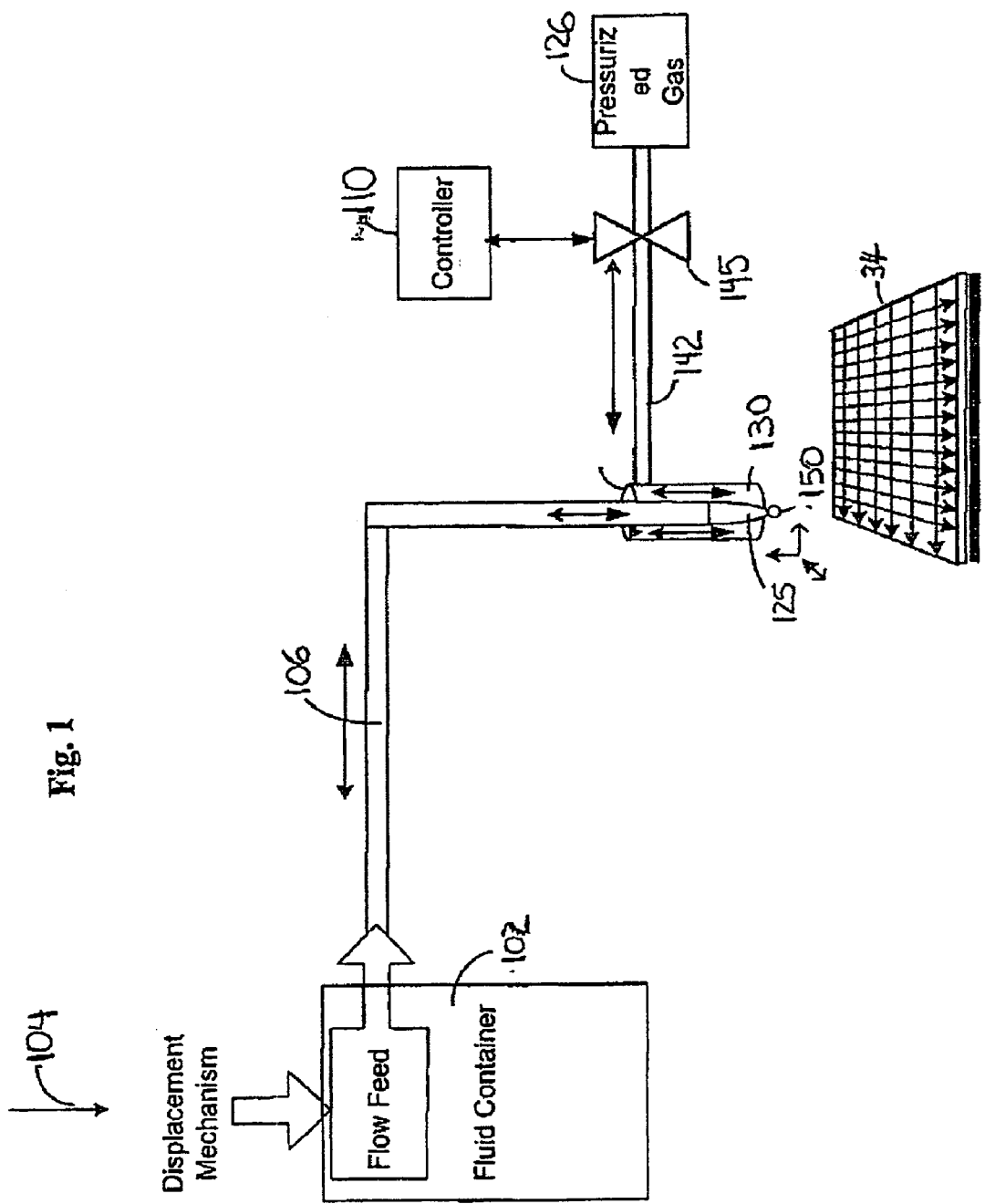

t = 0       t = 50ms    t = 75ms    t = 100ms t = 0       t = 50ms    t = 75ms    t = 100ms

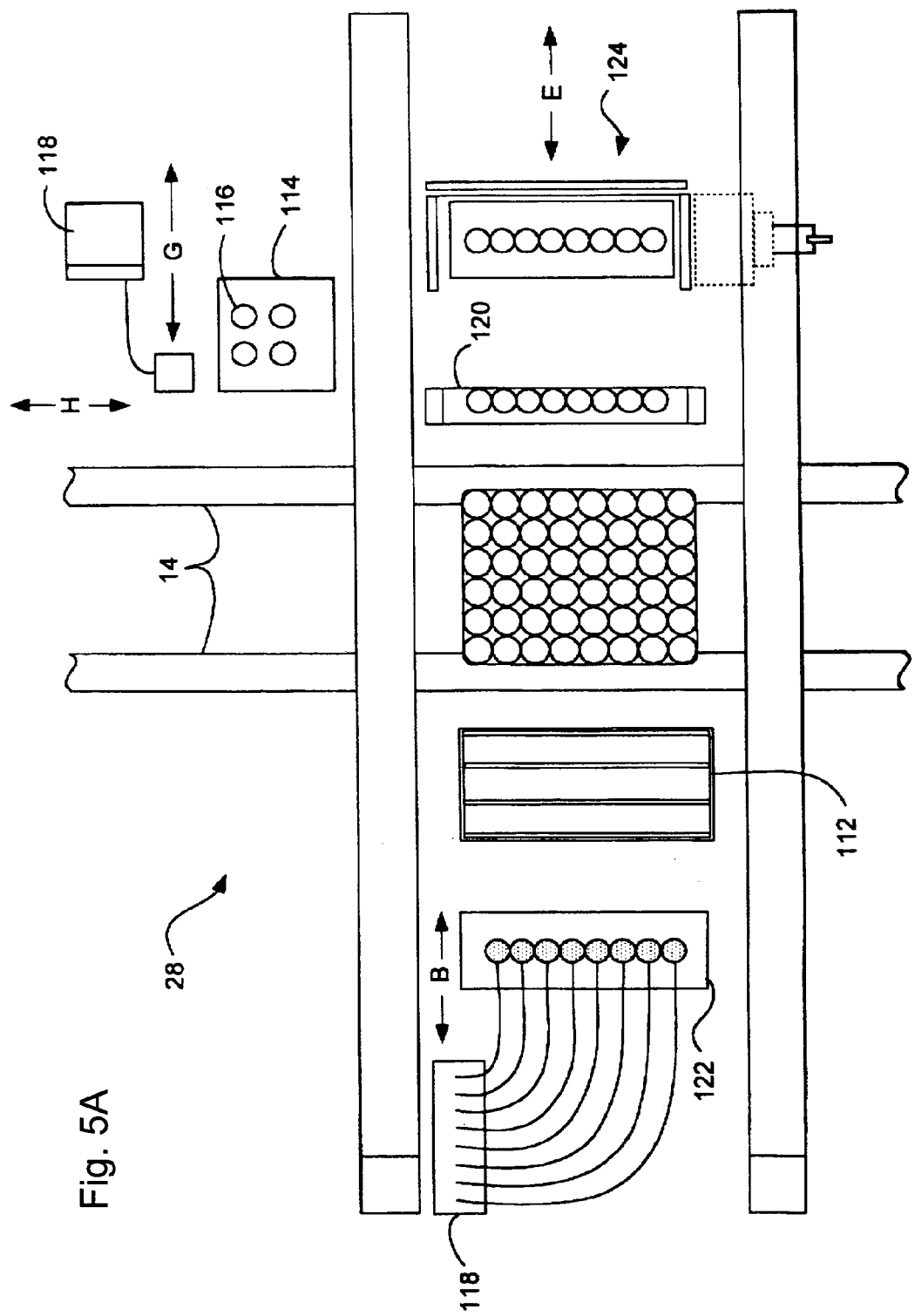

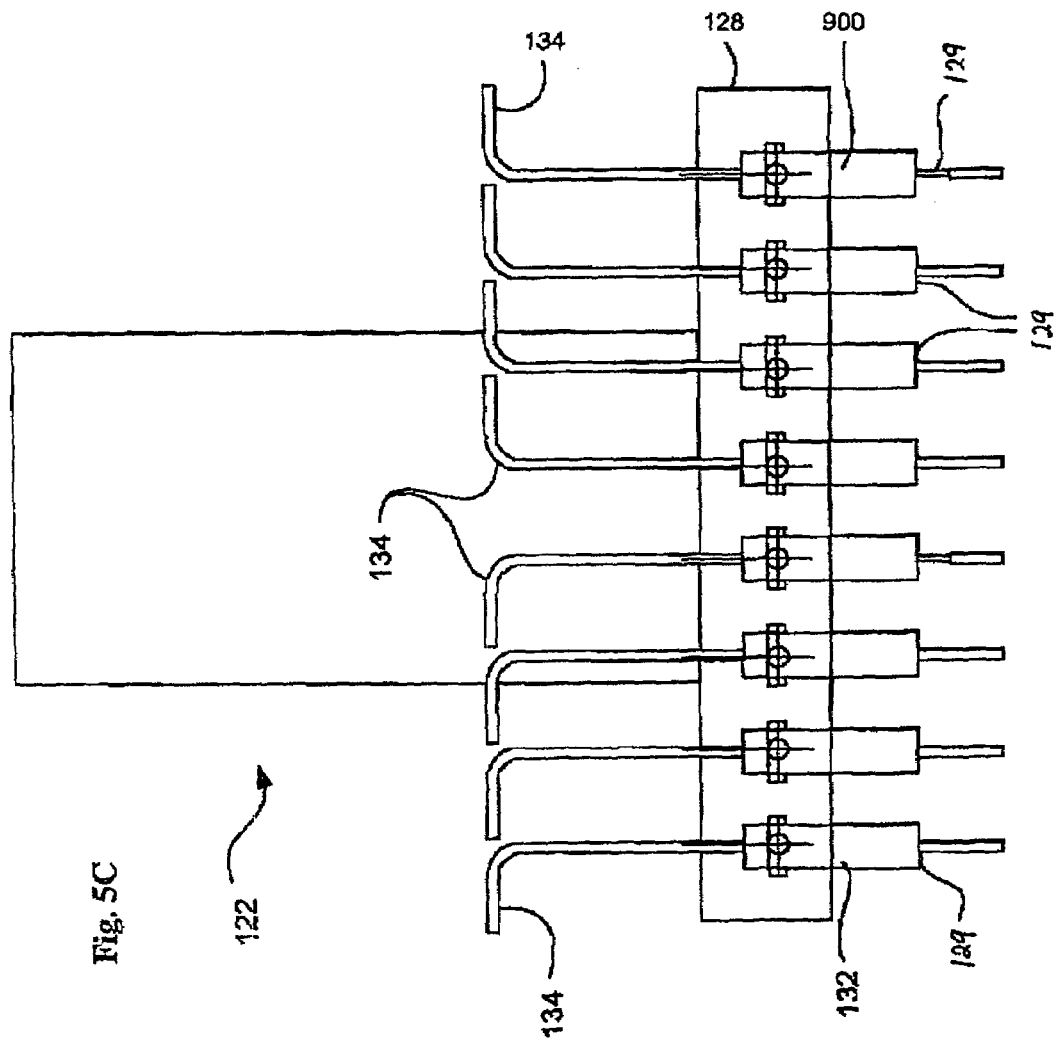

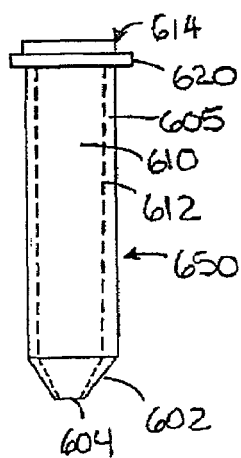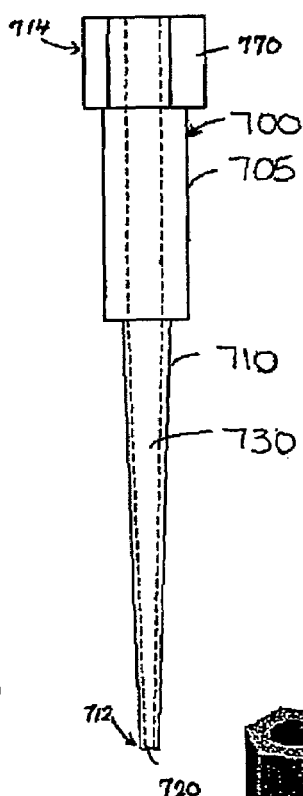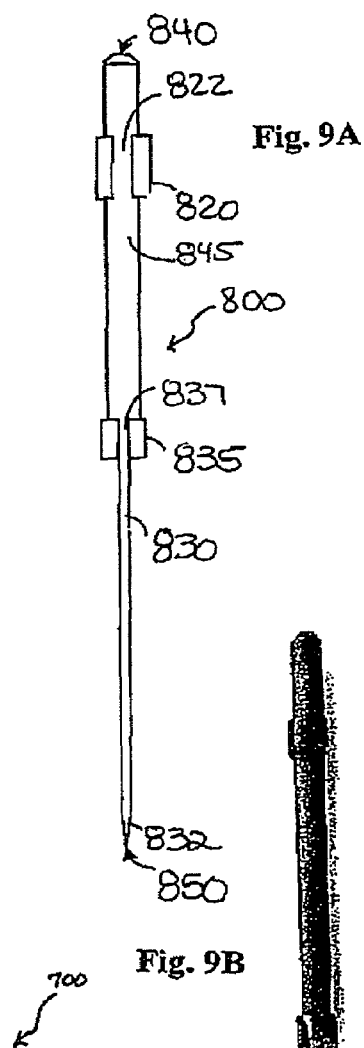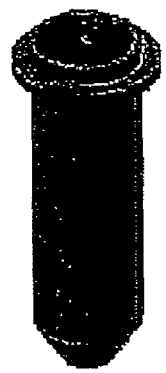

SMALL VOLUME LIQUID HANDLING APPARATUS AND METHOD

BACKGROUND OF THE INVENTION

1. Field of the Invention

The present invention relates to methods and apparatus for dispensing volumes of liquids and, more particularly, to methods and apparatus for automating dispensing liquid volumes.

2. Description of the Related Art

There are numerous applications where dispensing small volumes of liquids is useful. As used herein, unless further specified, a small volume refers to a volume less than 10 microliters, and optionally less than 1 microliter. For example, U.S. Pat. No. 6,296,673, which is incorporated herein by reference, describes performing experiments where less than 1 microliter of liquid is dispensed in order to determine crystallization conditions for molecules, particularly for proteins.

Repeatably dispensing reagents or other fluids with precision and accuracy can be a difficult task, particularly as the volume of liquid delivered decreases, as viscosity increases, and when what is dispensed varies experiment to experiment. For example, as indicated in U.S. Pat. No. 6,296,673, the composition of the liquids dispensed may stay the same or may vary experiment to experiment. Meanwhile, the viscosities and other flow properties of the reagents being dispensed can vary reagent to reagent. These variances become more technically significant and challenging as the volume that is dispensed decreases.

Several commercial low volume liquid dispensers are available, including, for example: Beckman Colter Corporation, including the Biomek FX and the Multimek 96/384 models; Zymark Corporation, including the Rapid Plate® models 96/384 microplate pipetting work station and the Sciclone ALH (advanced liquid handler) work station; Packard Bioscience, including the Multiprobe II and EX models and Multiprobe II HT and EX models; Robbins Scientific, including the Hydra Microdispensers; and Gilson Corporation, including the 215 liquid handler work station. These systems are examples of industry standard robot liquid handling systems that have been used to automate many different kinds of experimental procedures.

The above mentioned systems typically include a dispensing mechanism that is moved relative to a platform that can hold wide variety of substrates for receiving liquid, including 96-well, 384-well, and 1536-well microliter plates, tubes, vials, glass lights, reservoirs, etc. For example, the dispensing equipment may include a dispensing head mounted on or in association with a programmable X, X-Y or X-Y-Z table or carriage. The motion of the table may be electronically coordinated with the operation of the dispensing mechanism so that the dispenser can be caused to dispense volumes of reagent or other fluid at any one of a number of locations defined by the position of the X and Y axes of the X-Y table. In operation, the X-Y table moves the dispensing head to a desired location and then stops while the dispenser is caused to dispense an amount of reagent onto a location of the substrate at the desired location. After each dispensing operation is completed, the X-Y table then moves to the next location and the process repeats for as many locations as are necessary to complete the pattern. In some instances, the X-Y table does not come to a stop but rather continuously moves as fluid is dispensed. It is noted that the X-Y table may also be used to move the substrate relative to the dispensing mechanism.

Many of the existing dispensing methods and equipment possess limitations regarding their precision, accuracy and durability. As the volume of liquid that needs to be delivered for experimental procedures decreases and the demand for throughput increases, a need will continue to exist for more effective dispensing technologies.

One application for dispensing small volumes of liquids that is particularly relevant to Applicants' research is the crystallization of molecules, and particularly biomolecules, such as proteins. Applicants perform a great many crystallization experiments on proteins in conjunction with its structural biology and drug discovery research. For example, in the last 12 months, Applicants have used dispensing technology to set up more than 3 million protein crystallization experiments. Integral to these experiments is the dispensing of liquids at volumes less than 1 microliter. By performing so many crystallization experiments, Applicants have realized certain functional, reliability and durability limitations with existing dispensing technology. The dispensing technology described herein seeks to remedy these limitations.

SUMMARY OF THE INVENTION

Methods and apparatus are provided for delivering small volumes of fluid to a substrate. The small volume delivered may be less than 10 microliters, optionally less than 5 microliters, optionally less than 2 microliters, optionally less than 1 microliter, optionally less than 500 nanoliters, and optionally less than 250 nanoliters.

In one embodiment, a fluid dispenser head is provided comprising: a dispensing head through which an aliquot of liquid is delivered to a distal end of the dispensing head where the aliquot of liquid is retained; and a pressurized gas displacement mechanism which delivers an aliquot of gas to the distal end of the dispensing head which causes the aliquot of liquid retained at the distal end of the dispensing head to separate from the distal end of the dispensing head.

In another embodiment, a fluid dispensing system is provided comprising: a fluid container; a dispensing head in fluid communication with the fluid container; a displacement mechanism which delivers fluid from the fluid container to the dispensing head such that an aliquot of liquid is delivered to a distal end of the dispensing head where the aliquot of liquid is retained; and a pressurized gas displacement mechanism which delivers an aliquot of gas to the distal end of the dispensing head which causes the aliquot of liquid retained at the distal end of the dispensing head to separate from the distal end of the dispensing head.

According to each of the above embodiments, the displacement mechanism may be a mechanical displacement mechanism. For example, the displacement mechanism may optionally be selected from the group consisting of a syringe, a pump, an electrophoretic device and a mechanical displacement device.

Also, according to each of the above embodiments, the displacement mechanism may deliver the aliquot of liquid such that it is retained by the distal end of the dispensing head due to surface tension between the liquid and the distal end of the dispensing head.

Also, according to each of the above embodiments, the dispensing head may define a lumen through which the aliquot of fluid is delivered. The dispensing head may also define a gas housing through which the aliquot of gas is delivered to the distal end of the dispensing head. The dispensing head may also include a needle positioned within the lumen that extends beyond the distal end of the lumen.

Also, according to each of the above embodiments, the dispensing head may define a lumen through which the aliquot of fluid is delivered, the lumen being surrounded by an outer gas housing through which the aliquot of gas is delivered to the distal end of the dispensing head.

Also, according to each of the above embodiments, the aliquot of liquid dispensed has a volume of less than 1 microliter and preferably 500, 250, 200, 100 nanoliters or less.

Also, according to each of the above embodiments, the pressurized gas displacement mechanism may control the energy supplied by the aliquot of gas within a range of 0.001 W to 100 W.

Also, according to each of the above embodiments, the pressurized gas displacement mechanism may control the weight of the aliquot of gas released within a range of $10^{-10}$ W to about $10^{-4}$ kg.

Also, according to each of the above embodiments, the pressurized gas displacement mechanism may control the pressure of the aliquot of gas released within a range of 0.05 psi to 50 psi.

Also, according to each of the above embodiments, the pressurized gas displacement mechanism may cause the aliquot of liquid to be dispensed without aerating the aliquot of liquid. As a result, an aliquot of liquid is formed on a substrate.

Also, according to each of the above embodiments, the fluid dispensing system may further comprise a pressurized gas source regulated by a flow valve to the dispensing head.

Also, according to each of the above embodiments, the fluid dispensing system may further comprise a controller that actuates the flow valve to release a discontinuous aliquot of gas.

Also, according to each of the above embodiments, the fluid dispensing system may further include a controller coupled to actuate a gas supply coupled to the pressurized gas displacement mechanism.

Also, according to each of the above embodiments, the pressurized gas displacement mechanism may comprise a solenoid valve.

Also, according to each of the above embodiments, the fluid dispensing system may further include a controller coupled to actuate a solenoid valve of the pressurized gas displacement mechanism.

Also, according to each of the above embodiments, the fluid dispensing system may further include a controller comprising a timer circuit which times operation of the pressurized gas displacement mechanism relative to operation of the displacement mechanism.

Also, according to each of the above embodiments, the fluid dispensing system may further include a controller comprising a timer circuit which operates the pressurized gas displacement mechanism to release an aliquot of gas after operation of the displacement mechanism.

Also, according to each of the above embodiments, the fluid dispensing system may comprise a plurality of dispensing heads and a mounting block configured to provide gas supply bores to supply gas to each of the plurality of dispensing heads.

Also, according to each of the above embodiments, the fluid dispensing system may comprise at least one gas control solenoid coupled between the displacement mechanism and the pressurized gas displacement mechanism.

Also, provided are various methods for dispensing fluid. In one embodiment, a fluid dispensing method is provided comprising: delivering an aliquot of liquid having a volume of less than 1 microliter through a distal end of a dispensing head such that the aliquot of liquid is retained by the distal end of a dispensing head; and delivering an aliquot of gas to the distal end of the dispensing head after delivery of the aliquot of liquid to cause the aliquot of liquid otherwise retained by the distal end of the dispensing head to separate from the distal end of the dispensing head.

According to this embodiment, the aliquot of gas is optionally delivered within a lumen of the dispensing head to the aliquot of fluid.

Also, according to this embodiment, the dispensing head optionally defines a lumen through which the aliquot of fluid is delivered and a needle is positioned within the lumen that extends beyond the distal end of the lumen, the aliquot of liquid being retained by the needle, the aliquot of gas causing the aliquot of liquid to separate from the needle.

Also, according to this embodiment, the aliquot of gas is optionally delivered circumferentially around the aliquot of liquid.

Also, according to this embodiment, the aliquot of liquid dispensed optionally has a volume of less than 1 microliter.

Also, according to this embodiment, the energy supplied by the aliquot of gas optionally is within a range of 0.001 W to 100 W.

Also, according to this embodiment, the weight of the aliquot of gas released is optionally within a range of $10^{-10}$ to about $10^{-4}$ kg.

Also, according to this embodiment, the aliquot of gas released is optionally within a range of 0.05 psi to 50 psi.

Also, according to this embodiment, the aliquot of liquid is optionally dispensed without aerating the aliquot of liquid.

Also, according to this embodiment, a timer circuit may optionally be employed to control the timing of when the aliquot of gas is released relative to the formation of the aliquot of liquid.

Aspects of the present invention, particularly the controller, can be accomplished using hardware, software, or a combination of both hardware and software. The software used for the present invention is stored on one or more processor readable storage media including hard disk drives, CD-ROMs, DVDs, optical disks, floppy disks, tape drives, RAM, ROM or other suitable storage devices. In alternative embodiments, some or all of the software can be replaced by dedicated hardware including custom integrated circuits, gate arrays, FPGAs, PLDs, and special purpose computers.

These and other objects and advantages of the present invention will appear more clearly from the following description in which the preferred embodiment of the invention has been set forth in conjunction with the drawings.

BRIEF DESCRIPTION OF THE DRAWINGS

The invention will be described with respect to the particular embodiments thereof. Other objects, features, and advantages of the invention will become apparent with reference to the specification and drawings in which:

FIG. 1 is a block diagram illustrating the general structure of a fluid delivery device.

FIG. 3A illustrates the status of an apparatus delivering a small volume drop using a prior art apparatus at t=0 ms.

FIG. 3B illustrates the status of an apparatus delivering a small volume drop using a prior art apparatus at t=50 ms.

FIG. 3C illustrates the status of an apparatus delivering a small volume drop using a prior art apparatus at t=75 ms.

FIG. 3D illustrates the status of an apparatus delivering a small volume drop using a prior art apparatus at t=100 ms.

FIG. 4A illustrates the status of an apparatus delivering a small volume drop using an apparatus according to the present invention at t=0 ms.

FIG. 4B illustrates the status of an apparatus delivering a small volume drop using an apparatus according to the present invention at t=50 ms.

FIG. 4C illustrates the status of an apparatus delivering a small volume drop using an apparatus according to the present invention at t=75 ms.

FIG. 4D illustrates the status of an apparatus delivering a small volume drop using an apparatus according to the present invention at t=100 ms.

FIGS. 5A through 5E illustrate various stations which can be included in a volume delivery system according to the present invention.

FIG. 5A is a top view of a volume delivery station.

FIG. 5B is a side view of a volume delivery station.

FIG. 5C is a side view of a pipette holder.

FIG. 5D is a side view of a well cover holder.

FIG. 5E is a side view of a well cover magazine for storing well covers to be positioned over wells in a multi-well plate.

FIGS. 7A and 7B illustrate a gas nozzle structure used in the deposition assembly of the present invention.

FIG. 8A is a side view and FIG. 8B is a perspective view of a pipette used in accordance with the present invention.

FIG. 9A is a side view and FIG. 9B is a perspective view of a needle used in the deposition tip assembly of the present invention.

FIG. 15A illustrates a well of a multi-well plate in which a hanging drop crystallization experiment has been set up.

FIG. 15B illustrates a volume delivery station in a rest position.

FIG. 15C illustrates a pipette holder moved into a position over a well cover holder.

FIG. 15D illustrates the pipette holder returned to its rest position and a protein delivery pipette moved into position over a well cover.

FIG. 15E illustrates the protein delivery pipette moved into its rest position and the cover holder inverted and moved into position over the column of wells on the multi-well plate.

FIG. 15F illustrates hanging drops suspended from well covers over the wells of a plate.

FIG. 15G illustrates the cover holder moved into position over a well cover storage component.

FIG. 16A illustrates a well of a multi-well plate in which a sitting drop crystallization experiment has been set up.

FIG. 16B illustrates a volume delivery station in a resting position.

FIG. 16C illustrates the pipette holder moved into position over a column of wells in the multi-well plate.

FIG. 16D illustrates the pipettes in the pipette holder aligned with the sitting drop regions of wells in a column of the plate.

FIG. 16E illustrates the protein delivery pipette moved into position over the sitting drop region of a well in the column of wells in the multi-well plate.

FIG. 16F illustrates a sitting drop formed in the sitting drop region of a well.

DETAILED DESCRIPTION

Figure 2A:
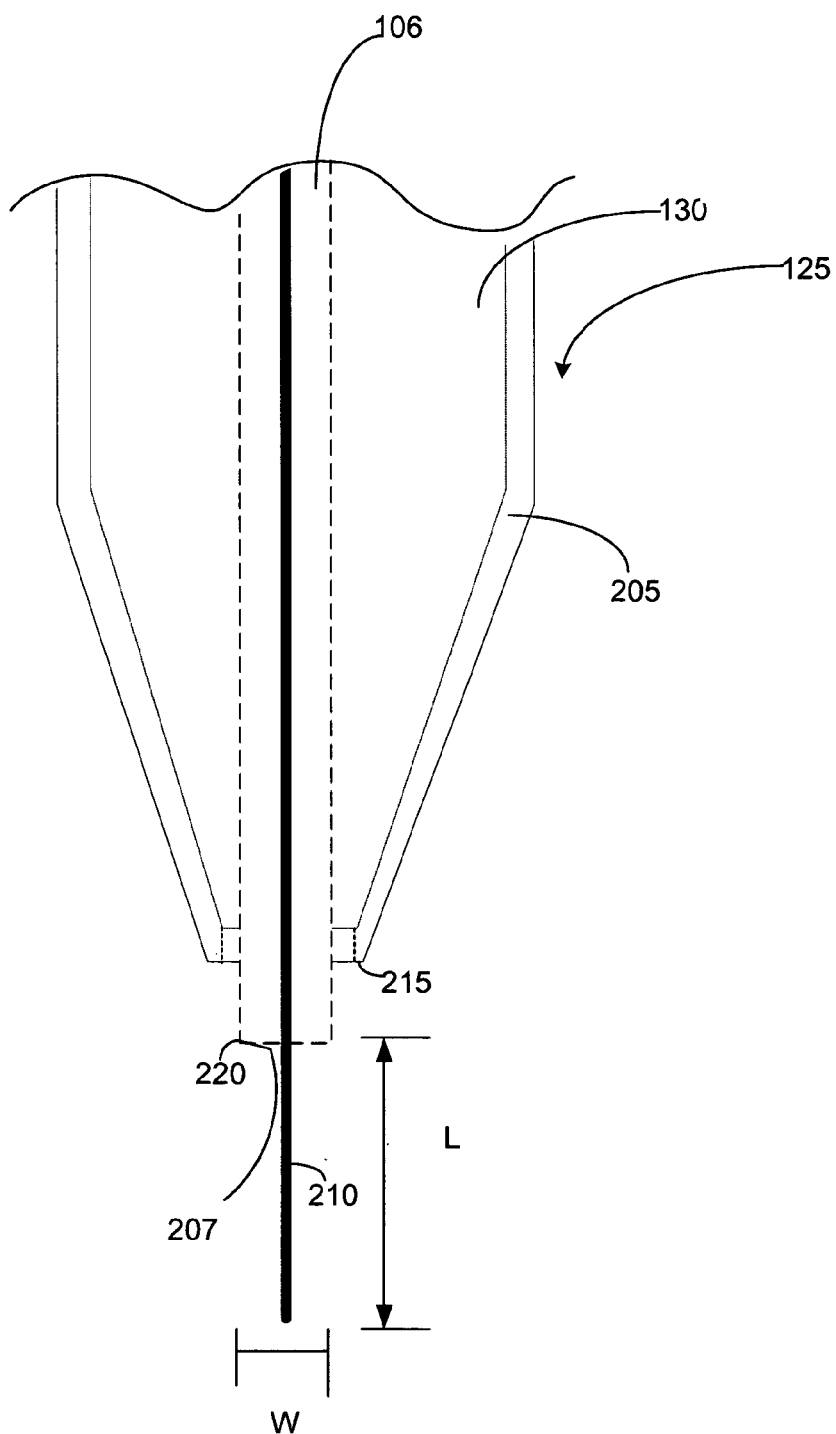
FIG. 2A shows a cross sectional view of a dispensing tip according to the present invention.

Various embodiments of a dispensing tip, controller, and small volume dispensing system of the present invention are hereinafter described. In accordance with the invention, a small volume of a liquid (an "aliquot of liquid") is dispensed onto a substrate. It is noted that the aliquot of liquid delivered is distinguished from the continuous delivery of liquid. Specifically, delivering an aliquot of liquid relates to delivering a discrete volume of liquid as opposed to a continuous stream of liquid.

The substrate may be any surface or vessel (such as a test strip, a cover slip, a slide, or a well of a multiwell plate) that one may wish to dispense an aliquot of liquid to as part of an experimental procedure. The aliquot of liquid dispensed may be any liquid that needs to be dispensed onto the substrate pursuant to an experimental procedure to be performed.

It will be recognized by the teaching herein that the dispensing tip of the present invention has particular applicability for the experimental systems described herein. However, it should also be recognized that the dispensing tip of the present invention has more general applicability to the dispensing and deposition of any liquid substance onto any substrate. In this regard, it should be further noted that existing systems for dispensing small volumes can be retrofitted using the dispensing tip and techniques taught herein to improve the precision, accuracy and durability of those systems.

One feature of the present invention is the use of an aliquot of gas delivered adjacent to the distal end of the dispensing tip to cause the aliquot of liquid to separate from the dispensing tip so that the aliquot of liquid is delivered to the substrate. It is noted that the aliquot of gas is not delivered to the distal end of the dispensing tip via the same lumen through which the aliquot of liquid is dispensed by the dispensing tip. Rather, in one variation, the aliquot of gas is delivered via a lumen that is external to the lumen that the aliquot of liquid is dispensed. Optionally, the aliquot of gas is delivered via a lumen that surrounds the lumen through which the aliquot of liquid is dispensed from the dispensing tip.

The direction and velocity with which the aliquot of liquid is dispensed from the dispensing system to the substrate can be controlled by the direction of gas aliquot incident on the aliquot of liquid. Variables of direction and velocity can be controlled by the size and aerodynamic profile of an inner gas chamber through which the gas aliquot passes before impacting the aliquot of liquid, the velocity and hence the force that the gas aliquot applies to the aliquot of liquid, and the length of time that the gas is supplied and hence the length of time that the force is applied against the aliquot of liquid.

A major advantage of the dispensing tip of the present invention is that it can dispense small volumes of highly viscous solutions. Prior art systems that use valves and solenoids to control liquid flow have difficulty opening and closing when submerged in highly viscous solutions. These solenoids can become clogged and/or corroded, thus requiring their replacement. By contrast, the dispensing tips provided herein do not have liquid come into contact with a solenoid valve, thereby eliminating a mechanical frailty observed in some prior art systems. In addition, the dispensing tips reduce the costly consumption of components (e.g. the clogged and corroded solenoids) that otherwise occurs with prior art systems.

FIG. 1 shows an overview of a system according to the present invention that incorporates a dispensing tip for depositing small volumes of a liquid with the assistance of an aliquot of gas. In FIG. 1, a fluid container 102 is provided. The fluid container contains a liquid that is to be dispensed onto a surface of a substrate in small volume aliquots. A displacement mechanism 104 is provided to ensure that the liquid in container 102 follows a fluid flow path 106 to a dispensing head 125. Examples of displacement mechanisms 104 that may be used include a syringe, a pump or electrophoresis. In an alternative embodiment, mechanical displacement is accomplished by the force of gravity.

The fluid flow path 106 may comprise a tubing network that provides the liquid to a dispensing head 125. The pressure of the liquid in flow path 106 is selected such that a small volume, shown as drop 150, will form at the end of dispensing head 125. The pressure is selected so that the aliquot of liquid is not forced off the tip, but retains its position at the distal end of head 125 due to surface tension.

In order to cause the aliquot of liquid 150 to separate from the dispensing head and travel to a substrate, such as multi-well plate 34, a pressurized gas is allowed in a flow path 142 through the dispensing head 125 to force the aliquot of liquid 150 from the dispensing head 125. The gas is controlled by a controller 110 from a pressurized gas source 126 regulated by a flow valve 145 to the dispensing head 125. When dispensing of drop 150 is desired, controller actuates valve 145 to release a puff of gas sufficient to force the aliquot of liquid 150 from the dispenser head 125 onto the substrate.

Figure 2B:
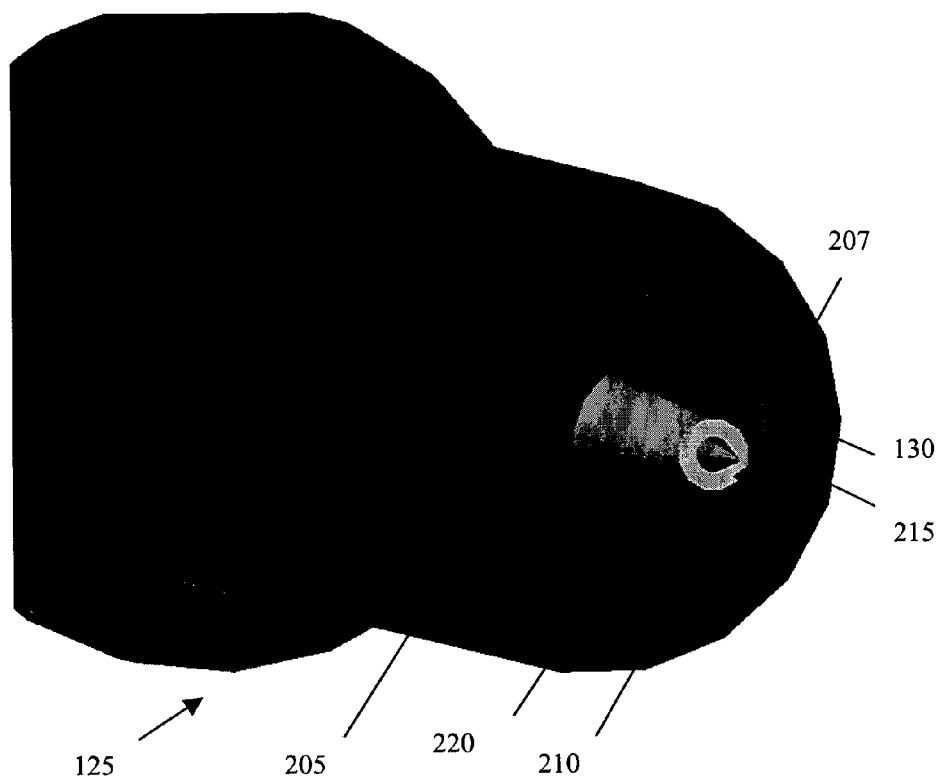
FIG. 2B shows a view of the distal end of the dispensing tip shown in FIG. 2A.

FIGS. 2A and 2B show an embodiment of a dispensing head 125. FIG. 2A shows a cross sectional view of the dispensing head 125 while FIG. 2B shows a view of the distal end of the dispensing head 125.

As shown in FIG. 2A, an exemplary dispensing head 125 may include an inner fluid flow tube 220 defining lumen 106 through which fluid to be deposited is delivered. An interior needle 210 may optionally be provided within the lumen 106 of the inner fluid flow tube 220 that extends beyond the distal end orifice 207 of the inner fluid flow tube 220.

The inner fluid flow tube 220 is surrounded by an outer gas housing 205. Outer gas housing 205 provides a gas flow path 130 that has an opening 215 adjacent the distal end of the inner fluid flow tube 220.

The spatial relationships between the interior needle 210, the inner fluid flow tube 220 defining the lumen 106 and the outer gas housing 205 defining the gas flow path 130 and distal opening 215 can be better seen via the view of the distal end of the dispensing tip 125 shown in FIG. 2B.

In the embodiment shown in FIGS. 2A and 2B, an interior needle 210 is provided that protrudes some distance "L" beyond the distal end of the inner fluid flow tube 220 through the orifice 207 formed by the lumen 106 of the inner fluid flow tube 220. Fluid traverses the inner flow path lumen 106 until it reaches the distal end of the inner fluid flow tube 220. The needle 210 allows a small volume drop corresponding to the fluid dispensed through the inner flow path lumen 106 to form on the needle 210 distal to the distal end of the fluid flow tube 220, creating a well-formed droplet that may later be blown off in a superior fashion.

Although a needle is not required, it has been found that the use of the needle allows greater control of the formation of small volume drops outside of the end of the fluid path lumen 106.

By optimizing the geometrical relationships between the orifice formed at the distal end of the inner flow path lumen, the length and diameter of the needle 210, and the gas flow path 130, the resolution of the dispensing liquid can be adjusted. In one embodiment, the needle may be eliminated, such that the size of the orifice 207 formed at the distal end of the inner flow path lumen provides the determining factors for droplet breakoff under the force of the supplied gas. It is believed that as the geometry of the respective elements of the dispensing head in FIGS. 2A and 2B are scaled down, the limiting factor for droplet size will be when the surface tension of the small volume drop requires blasts of gas that aerate the small volume drop such that the droplet splatters on contact with the target substrate or evaporates. It is noted that, in some applications, it may be desirable to allow splatter, aeration, or evaporation to occur and in such instances, these smaller drop volumes may be used.

FIGS. 3A through 3D show a time lapse sequence of a volume delivery in a system in accordance with the prior art that uses fluid pressure on the fluid in combination with physical contact with the substrate to cause a drop to separate from the end of a prior art dispensing head 310 shown therein.

Figures 3A, 3B, 3C, 3D:
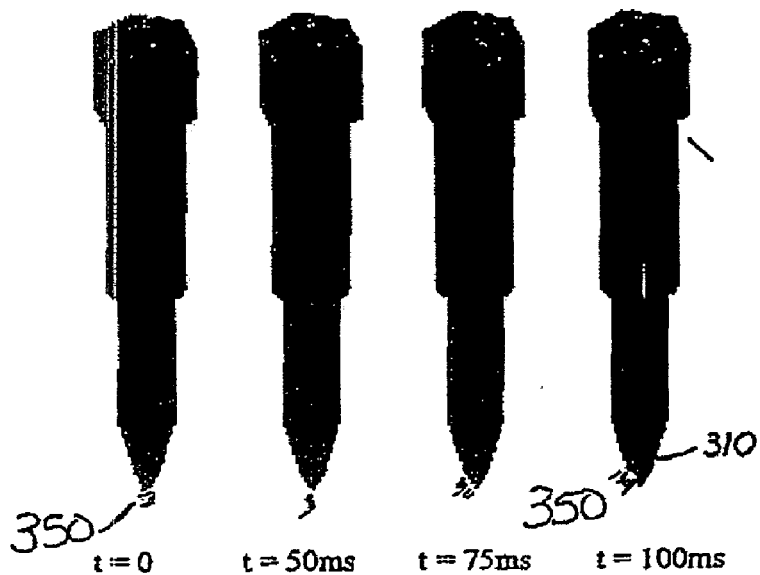
FIGS. 3A through 3D illustrate a process of delivering small volume drops using a solenoid actuated deposition tip in accordance with a prior art apparatus.

As shown in FIG. 3A, at time T-0, pressure exerted on a fluid flow path within dispensing head 310 will begin formation of a droplet 350 at the distal end of the dispensing head 310. At time T-1, shown in FIG. 3B, which is approximately 50 milliseconds beyond time T-0, the droplet will begin to disassociate from the distal end of the dispensing head under the weight of gravity and the momentum of the fluid dispensed from the dispensing head. At time T-2, approximately 75 milliseconds beyond time T-0, shown in FIG. 3C, surface tension between the fluid and the outer surface of the distal end of the dispensing head 310 will cause the aliquot of liquid to begin to adhere to the outer surface due to a variety of factors including fluid viscosity and loss of momentum of the dispensed fluid. Hence, in FIG. 3D, at time T-3, which is approximately 100 milliseconds beyond time T-0, drop 350 is shown adhered to the outer surface of the distal end of dispensing head 310. Because the droplet adheres to the outer surface of dispensing head 310, the droplet typically needs to be "touched off" in order to be transferred from the distal end of the dispensing head 310 to a substrate. Touching off requires that the dispensing head 310 physically engage a substrate or a mechanical object with sufficient surface tension to have the aliquot of liquid separate from the dispensing head to the substrate due to a combination of the surface tension of the mechanical object and the force of gravity.

By contrast, through the use of an aliquot of gas according to the present invention to assist separation of the small volume drop relative to the dispensing head, the need to touch off the aliquot of liquid is avoided. As a result, the present invention may be performed in a contactless fashion where the aliquot of liquid is not brought into contact with the substrate in order to transition the aliquot of liquid to the substrate.

FIGS. 4A through 4D show the dispensing of a drop in accordance with the present invention with the corresponding timeframe shown in FIGS. 3A through 3D.

Figures 4A, 4B, 4C, 4D:
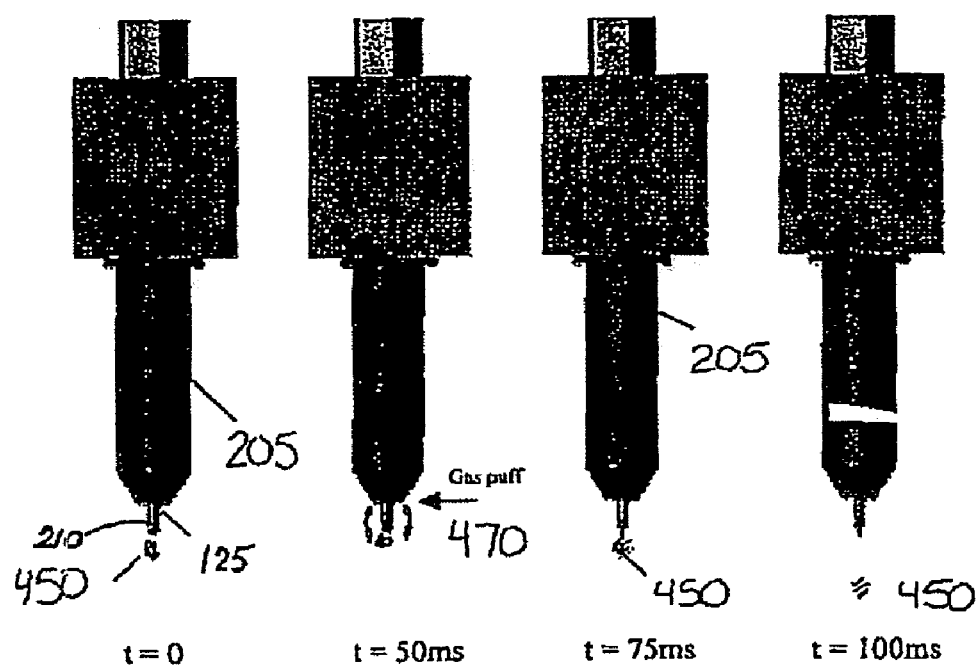
FIGS. 4A through 4D illustrate a time lapse sequence illustrating formation of a small volume drop in accordance with the deposition tip of the present invention.

In FIG. 4A, at time T-0, the dispensing head 125 has a drop 450 formed on the needle 210 protruding from the distal end of fluid flow housing 205. As shown in FIG. 4A, the aliquot of liquid is retained on the needle 210 by the inner adherence of the aliquot of liquid to the needle 210. At time T-1, a gas puff 470 is generated and expelled from the dispensing head so that, at time T-3 shown in FIG. 4C, drop 450 is forced off the end of needle 210 and in a direction toward a substrate. FIG. 4D shows that at time T-3, the aliquot of liquid may be a sufficient distance from the end of the dispensing head to reach a substrate positioned under the deposition tip.

In one embodiment, the outer diameter of the needle and the inner diameter of the orifice 207 formed by the lumen 106 of the inner fluid flow tube 220 has a ratio of 0.99 to 1. The range of the needle length L shown in FIGS. 2A and 2B extending from the distal end of the inner fluid flow tube 220 may be approximately 0.05 times to 1000 times the inner diameter of the orifice, optionally 1 to 10 times the inner diameter of the orifice. A typical diameter for the needle is between 0.005 inches and 0.04 inches. Accordingly, the needle length L may optionally be between 0.01 inches to 0.2 inches and optionally be between 0.05 inches to 0.1 inches.

The closer the ratio of the outer diameter of the needle to the inner diameter of the orifice approaches 1, the smaller the drop size yield. In one embodiment, no needle is used. When no needle is used, the inner diameter of the orifice alone determines the break-off size of the aliquot of liquid. As the geometry of the parts are scaled down, including orifice sizes and machine parts, eventually the limiting factor of the droplet size becomes the surface tension of the aliquot of liquid which requires a blast of gas to send droplets off at velocities that will scatter the droplet or cause it to evaporate. It is noted that droplet scatter and evaporation may be tolerated or even desired in certain applications.

The mass of gas needed for drop removal is typically between $1 \times 10^{-10}$ kg and $1 \times 10^{-4}$ kg, and may optionally be between $1 \times 10^{-9}$ kg and $1 \times 10^{-4}$ kg, $1 \times 10^{-8}$ kg and $1 \times 10^{-5}$ kg, and $1 \times 10^{-7}$ kg and $1 \times 10^{-5}$ kg. The quantity of gas needed will depend on the geometry and efficiency of the gas flow channels and the fluid viscosity. Gas pressure that may be expelled from the dispensing head to separate the fluid from the dispensing head may optionally be between 0.2 psi and 50 psi, optionally between 0.2 psi and 25 psi, or optionally between 0.5 psi and 10 psi. Ultimately, the pressure of the gas, and hence the velocity of the gas, will depend on the application and the properties of the liquid being dispensed. The energy requirement for the gas typically ranges from 0.001 w to 100 w, which, again, depends on geometry and efficiency of gas flow channels and fluid viscosity.

A variety of different gases may be used. The gas may contain oxygen, such as air, or may be an inert gas, such as nitrogen.

In one example, in order to cause an approximately 1 microliter-volume to separate from the tip, the approximate energy required is 0.271 W of energy, or 1.5 psi of pressure from an 0.08 in³ chamber of gas that is evacuated over a period of 50 milliseconds through a 0.15 inch diameter orifice. Assuming all potential energy is converted to kinetic energy, $3.15 \times 10^{-5}$ kg/s of gas (when gas=air) is used in this example to blow off the 1 microliter sized droplet. Since 50 milliseconds of gas flow is enough to cause the aliquot of liquid to separate, approximately $1.6 \times 10^{-6}$ kg of gas (assuming gas=nitrogen) is used in this example to blow off the droplet.

A general description of various protein crystallization setups including hanging and sitting drop crystallizations is provided a variety of references including McPherson, A. (1982) Preparation and Analysis of Protein Crystals, John Wiley and Son, New York, pp 82-127); Cox, M. J. and Weber, P. C. (1987) J. Appl. Cryst. 20:366; and Ward, K. B. et al. (1988) J. Crystal Growth 90:325-339.

FIGS. 5A-5E illustrate various stations that may be included in a volume delivery system for setting up hanging drop crystallizations. Although the volume delivery system illustrated in regard to FIGS. 5A-5E has been adapted for hanging drop crystallizations, it should be recognized that the volume delivery system can be readily modified for sitting drop crystallizations as well as other experimental procedures where it is desirable to deliver an aliquot of liquid.

Figure 5B:
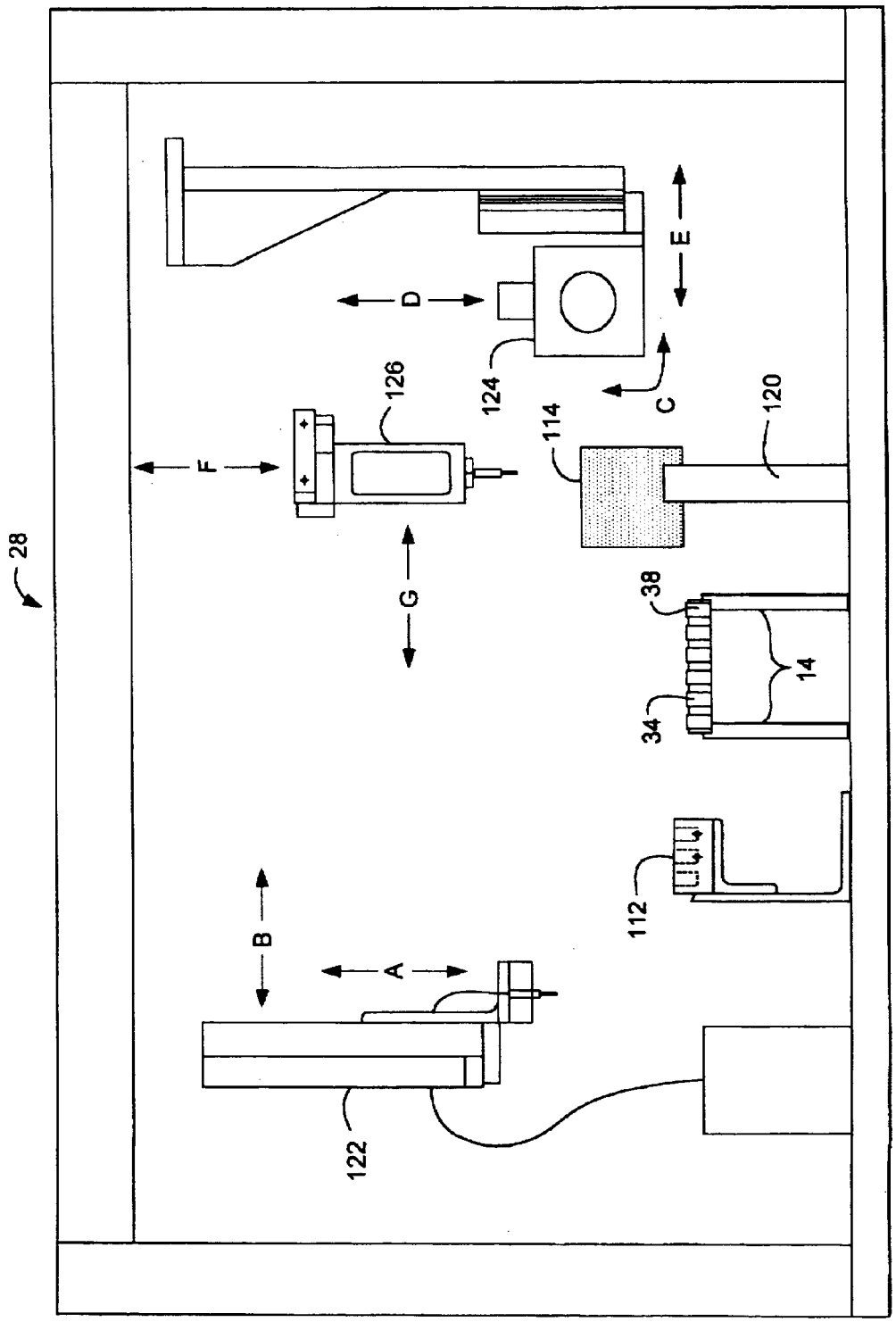

In regard to hanging drop crystallizations, FIG. 5A is a top view of a volume delivery station 28 and FIG. 5B is a side view of the volume delivery station 28. The volume delivery station 28 includes a wash basin 112 through which a cleansing solution can be flowed. Suitable cleansing solutions include, but are not limited to, water. The volume delivery station 28 also includes a molecule solution storage component 114 having one or more molecule solution wells 116 for storing solutions containing the molecule to be crystallized. The molecule solution wells 116 can be capped for storing the molecule solutions when the volume delivery system 28 is not in operation. The molecule solution storage component 114 can be refrigerated in order to provide cooling to the molecule solution within the molecule solution wells 116. For example, when the solution is a molecule solution, such as a solution of protein to be crystallized, the solution is preferably kept at 3-4° C. whether the volume delivery station 28 is or is not in operation. The volume delivery station 28 also includes syringe pumps 118 and a cover slip storage component 120 for storing cover slips.

The volume delivery station 28 also includes a dispenser assembly 122 configured to move vertically as indicated by the arrow labeled A and laterally as indicated by the arrow labeled B. The dispenser assembly's 122 lateral range of motion allows the dispenser assembly 122 to move to a variety of positions including a position over the wash basin 112 and a position over the cover slip holder 124. The volume delivery station 28 also includes a cover slip holder 124 configured to be inverted as indicated by the arrow labeled C. The cover slip holder 124 can move vertically as indicated by the arrow labeled D and laterally as indicated by the arrow labeled E. The dispenser assembly's 122 lateral range of motion allows the dispenser assembly 122 to move to a variety of positions including a position over the cover slip storage component 120 and several positions over the plate track 14. The volume delivery station 28 also includes a molecule delivery pipette 126 which is configured to move vertically as indicated by the arrow labeled F, laterally as indicated by the arrow labeled G and longitudinally as indicated by the arrow labeled H. The longitudinal and lateral ranges of motion allow the molecule delivery pipette 126 to be moved to a variety of positions including a position over each molecule solution well and a plurality of positions over the cover slip holder 124.

The above movements can be achieved by coupling the dispenser assembly 122, cover slip holder 124 and the molecule delivery pipette 126 to a variety of different actuators. Suitable actuators include, but are not limited to, pneumatic pistons, hydraulic pistons and a variety of motors.

FIG. 5C is a side view of a dispenser assembly 122. The dispenser assembly 122 includes a support frame 1100. The support frame 1100 holds a number of assemblies 129 equal to the number of wells 38 in a column of a multi-well plate 34. The assemblies 129 are held at a spacing which approximates the spacing between the wells 38 in the column of the multi-well plate 34. This spacing permits each assembly 129 to be concurrently aligned with a different well 38 in the column.

Each assembly is coupled to the fluid source and the fluid flow path may include a valve 132 and a conduit 134 extending from the valve 132 to a syringe pump 118. The syringe pump 118 can be used to provide the mechanical force described with respect to FIG. 1. Suitable valves 132 include, but are not limited to, piezoelectric valves and solenoid valves.

The pipette arrangement used for the molecule delivery pipette 126 is similar to the assembly arrangement used for the assemblies 129 within the dispenser assembly 122, except pipettes are substituted for the dispenser assemblies. The molecule delivery pipette 126 also includes a valve 132 and a conduit 134 extending from the valve 132 to a syringe pump 118. The molecule delivery pipette 126 is able to produce molecule solution drops less than 1 microliter and preferably 500, 250, 200, 100 nanoliters or less.

Figure 5D:
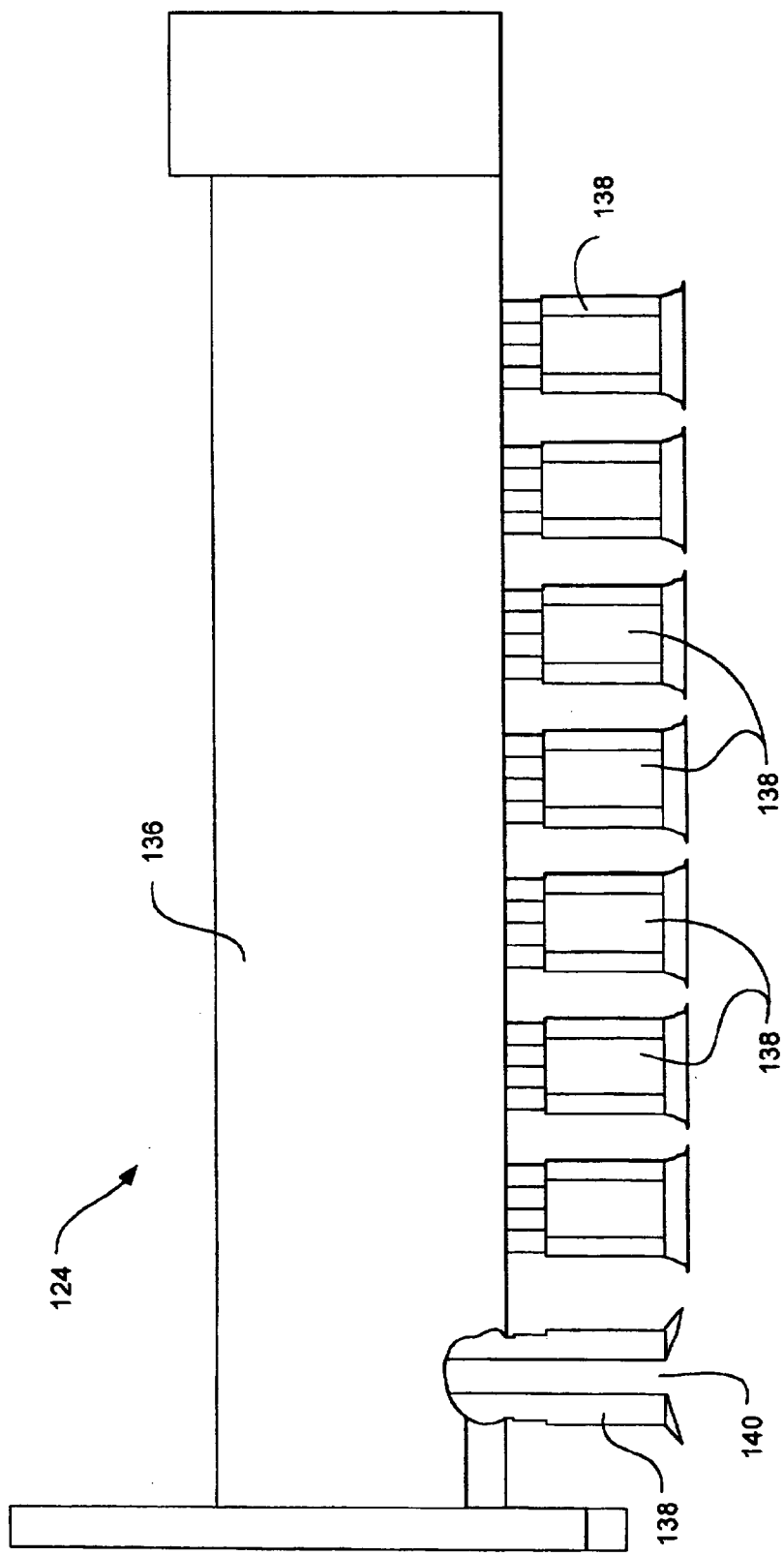

FIG. 5D is a side view of a cover slip holder 124. The cover slip holder 124 includes a frame 136 which supports a plurality of support cups 138 shaped to removably hold cover slips at a spacing which approximates the spacing between the wells 38 in a column of the multi-well plate 34. This spacing permits each cover slip to be concurrently aligned with a different well 38 in a column of the multi-well plate 34.

The support cups 138 can include an attachment mechanism 140 for immobilizing the cover slips in place relative to the support cups 138. The attachment mechanism 140 serves to keep the cover slips in place when the cover slip holder 124 is inverted. However, the attachment mechanisms 140 can release the cover slips at a desired moment. Suitable cover slip holder 124 attachment mechanisms 140 include, but are not limited to, a vacuum source in pneumatic communication with vacuum ports positioned in the support cups 138. Pulling a vacuum through the vacuum ports serves to keep the cover slips in place on the cover slip holder 124. However, when the cover slip holder 124 is inverted, the vacuum can be released by disengaging the vacuum source or reversing the vacuum. The release of the vacuum releases the cover slips from the cover slip holder 124.

Figure 5E:
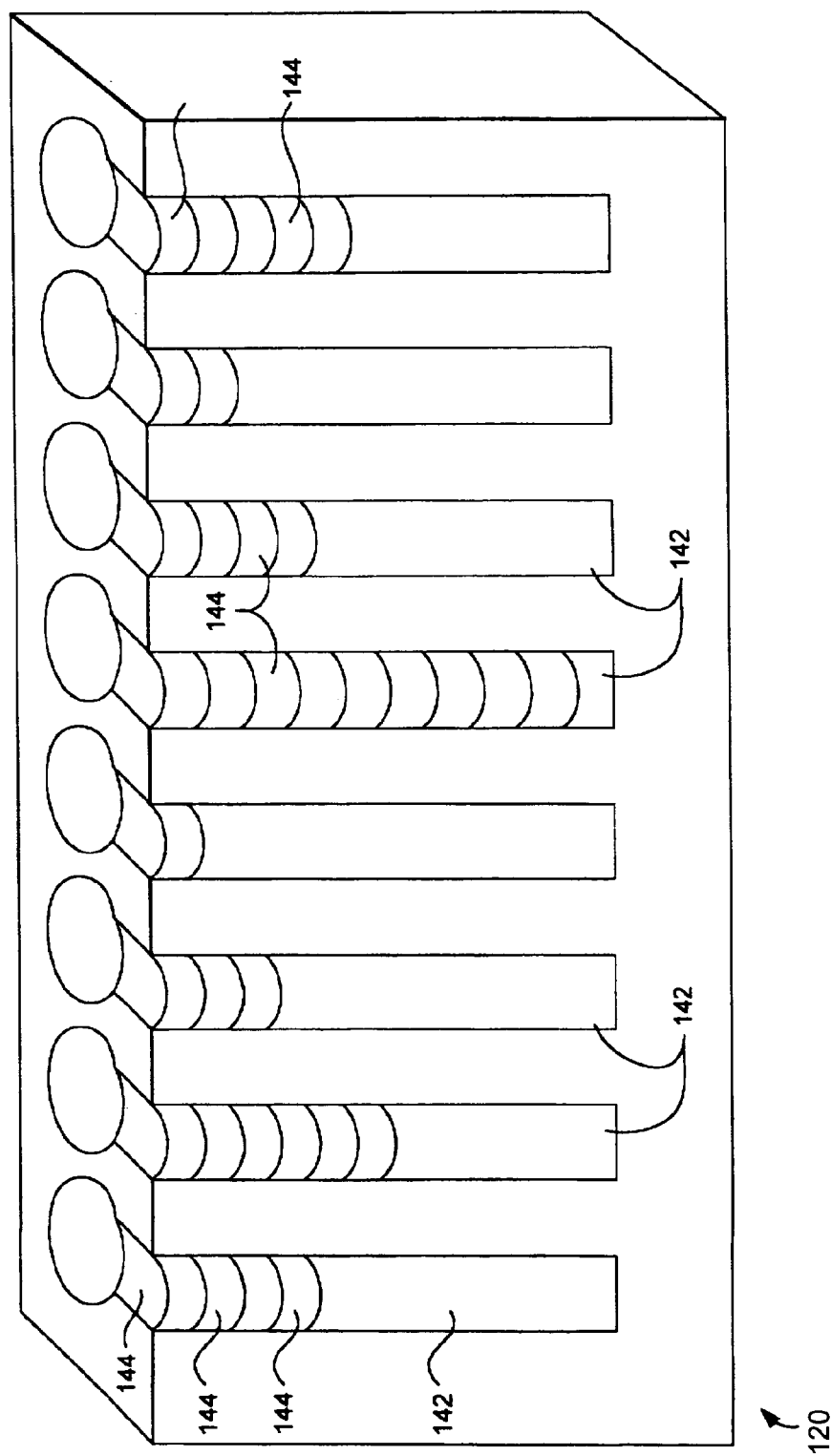

FIG. 5E is a side view of a cover slip storage component 120 which includes a plurality of magazines 142 sized to hold cover slips 144 stacked on top of one another. The stack of cover slips 144 within the magazine 142 can be biased upward until the cover slip 144 on the top of the stack is near the top of the magazine 142. The spacing between the magazines 142 approximates the spacing between the support cups 138 of the cover slip holder 124. This spacing permits each magazine 142 to be concurrently aligned with a different support cup 138 of the cover slip holder 124. Accordingly, a cover slip 144 from each magazine 142 can also be aligned with a different support cup 138.

Figure 6:
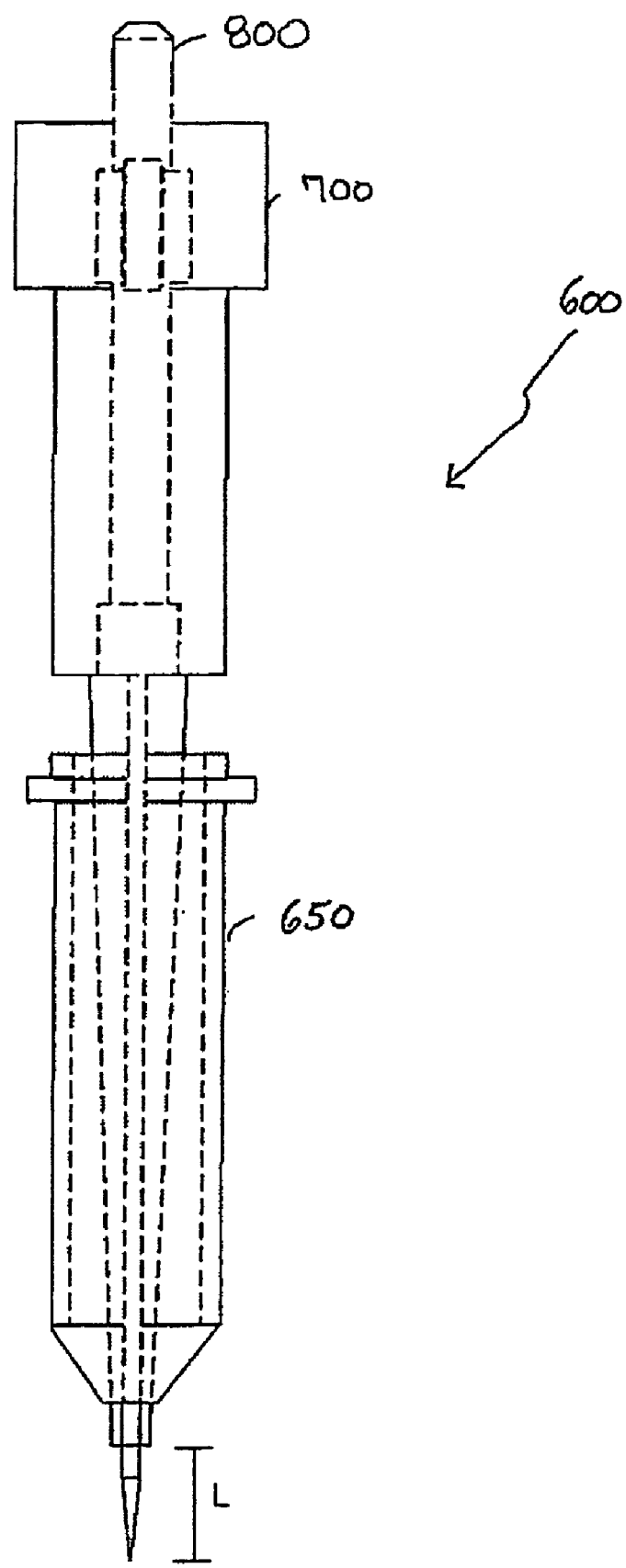
FIG. 6 is a cross-sectional view of one embodiment of the deposition tip assembly used in accordance with the present invention.

FIG. 6 shows an embodiment of a deposition assembly 600 and mounting block shown in FIGS. 5A-5E in additional detail where the deposition assembly incorporates a dispensing head according to the present invention. Assembly 600 generally includes a gas nozzle 650, a pipette 700, and a needle 800. Details of these particular components are shown in FIGS. 7A through 12B.

FIG. 7A is a side view, and FIG. 7B a perspective view, of the gas nozzle 650. Nozzle 650 includes a main body 605 that defines a lumen 610 formed therein. A distal end 602 of the lumen 610 of the gas nozzle 650 tapers to an orifice 604 through which the distal ends of pipette 700 and needle 800 extend. A flange 620 is positioned near the proximal end 614 of the gas nozzle 650 where it engages a gas block assembly shown and described with respect to FIGS. 10 A-B.

The lumen 610 formed by the main body 605 allows gas to pass between the interior wall 612 of the housing 605 and the exterior wall of the pipette 700 when the pipette is positioned within the lumen 610. The orifice 604 is sufficient so that gas passing through chamber 610 exits around the pipette 700.

FIG. 8A is a side view, and FIG. 8B a perspective view, of the pipette 700 shown in FIG. 6. Pipette 700 includes a proximal end 714, a distal end 712, and a lumen 730 extending from the proximal end to the distal end of the pipette 700 that forms orifice 720. The lumen 730 allows liquid to traverse the pipette between the interior wall of the lumen and the exterior wall of needle 800 when the needle is positioned within the lumen 730 and exit the distal end 712 of the pipette at orifice 720.

As shown in FIG. 6, needle 800 fits in the lumen 730 of pipette 700 and fluid passes through interior cavity 730 to the tip 710 of pipette 700. As shown in FIG. 6, needle 800 protrudes from the opening 720 of pipette 700.

FIG. 9A and FIG. 9B show a side view and a perspective view of needle 800. Needle 800 includes a first end 840 and a second end 850. A main body 845 has a thicker diameter than a needle shaft 830. Bushings 820 and 835 surround two portions of the main body 845. Each bushing 820, 835 includes an opening 822, 837, respectively, to allow fluid flow to pass between needle 800 and the interior cavity 730 of the pipette 700. Needle 800 has a tip 832 formed to a sharpened point.

Returning to FIG. 6, in operation, a fluid passes through interior cavity 730 of pipette 700 via openings 822 and 837 in bushings 820 and 835, respectively. These allow fluid flow around needle 800 to the tip at the orifice opening 720 of pipette 700, gas is provided to the interior chamber 610 of nozzle 650 on a selective basis to extract droplets formed on the needle tip 832 extending outside of orifice 720 of pipette 700.

Figure 10A:
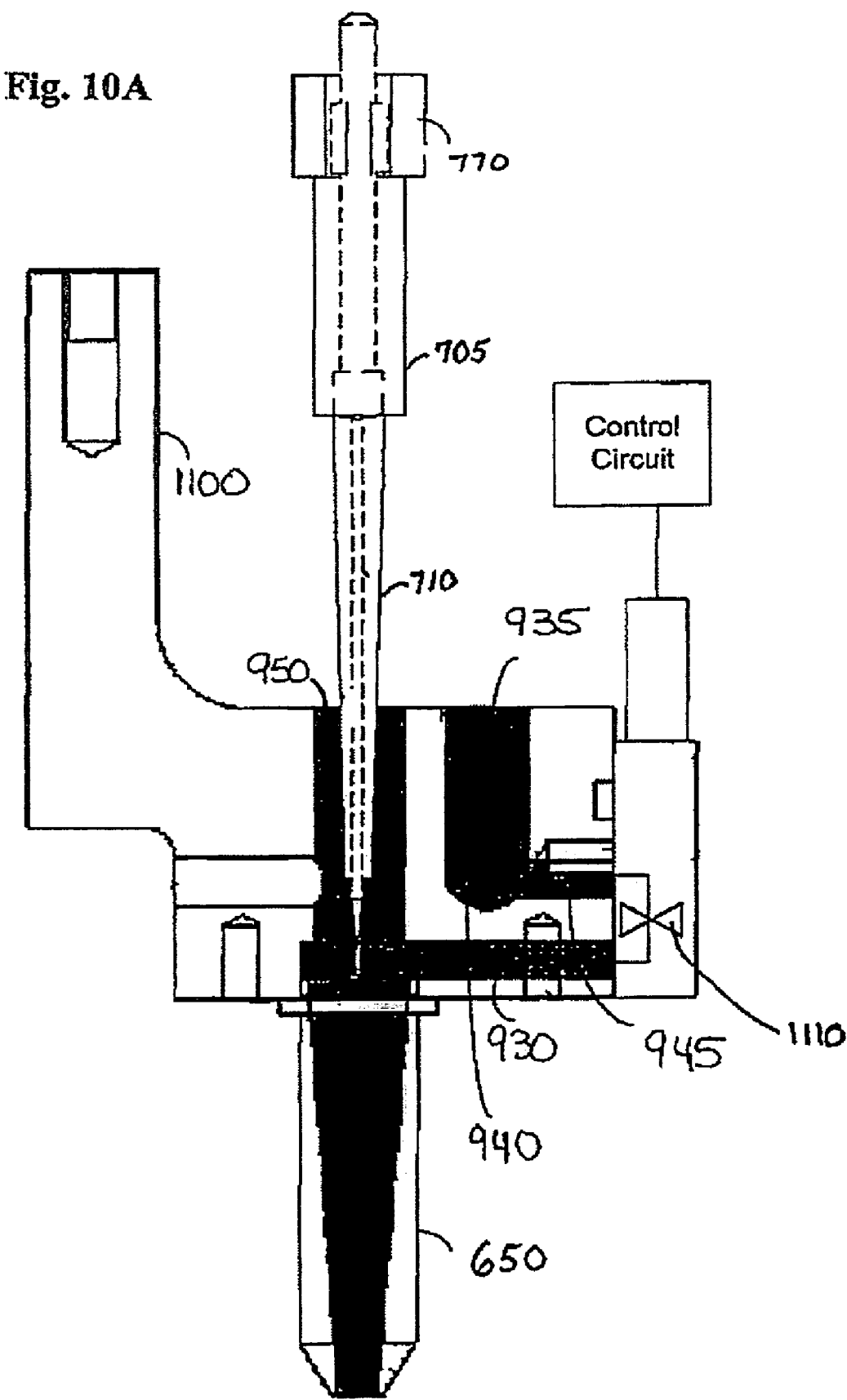
FIG. 10A shows a cross-sectional view of a gas network mounting block assembly suitable for securing multiple deposition assemblies.
Figure 10B:
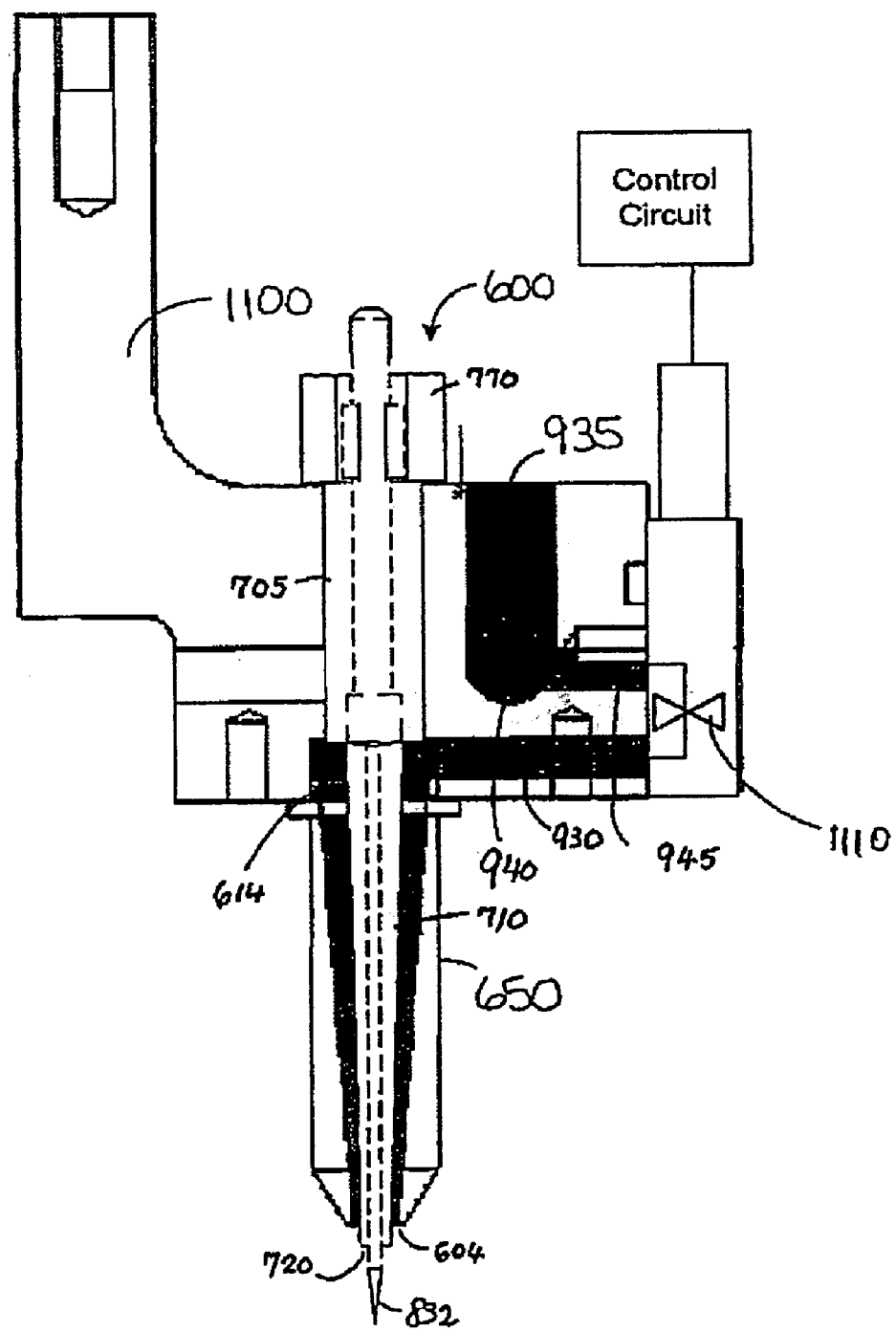
FIG. 10B shows a cross-sectional view of a gas network mounting block assembly suitable for securing multiple deposition assemblies.
Figure 11:
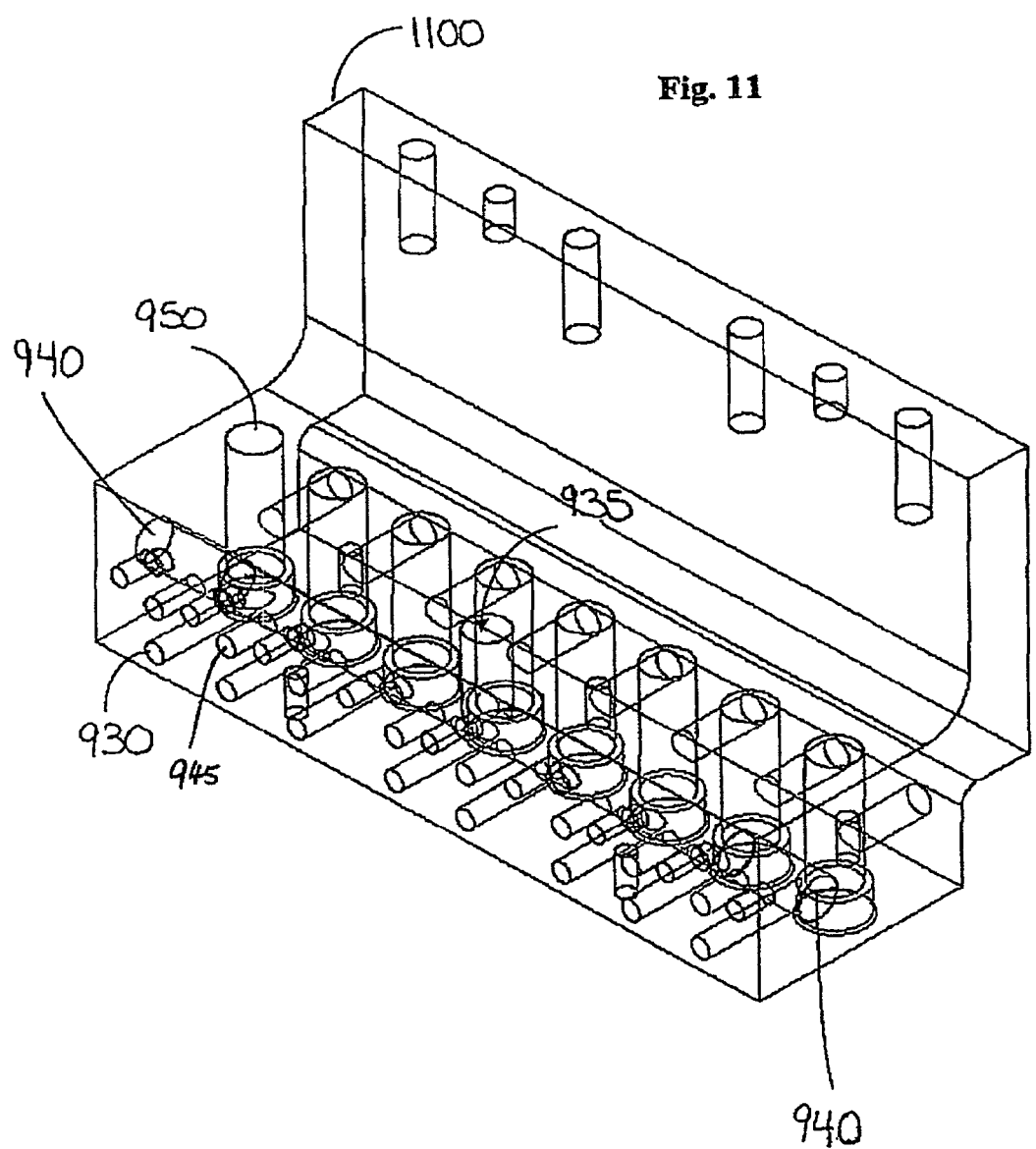
FIG. 11 shows a perspective view of a gas block mounting assembly.

FIGS. 10A, 10B and 11 show a gas network mounting block assembly suitable for securing multiple deposition assemblies 600 in a configuration which allows depositing small volumes into multi-well trays in, for example, a system such as that shown in FIGS. 14A through 14E.

FIGS. 10A and 10B are cross-sectional views and FIG. 11 is a perspective view of the gas network mounting block assembly. As shown in FIGS. 10A and 10B, main bore 950 formed in block 1100 allows for mounting the gas nozzle 650 and pipette 700 with needle 800 secured within pipette 700. Mounting block 1100 is sized so that the outer housing of pipette 700 sealably engages the interior of bore 950. Pipette is secured in the block by the net-shaped end 770 of pipette 700. Gas nozzle 650 is secured to the lower portion of block 1100 by having its proximal end 614 secured in bore 950. Proximal end 614 aligns with a gas flow cavity 930 formed in bore body 950. A threaded bore 912 is provided so that a securing bolt (not shown) may be inserted in bore 912 to secure pipette within mounting block 1100. Block 1100 may be formed of stainless steel or other suitable hard material.

FIG. 10B shows the entire assembly 600 mounted in block 1100. As shown therein, gas flow about the exterior of pipette tip 710 is provided via bore 950. The length of outer housing 705 of pipette 700 is configured so that it reaches to a point just above the entrance into bore 950 of a gas cavity 930 also formed in block 1100. A main gas feeding bore 935 feeds a cross-sectional bore 940 which runs the length of the block, as shown in FIG. 11. Bore 940 feeds gas through feeder bores 945 to each of a plurality of solenoids 1110 which are electrically coupled to a control circuit. The solenoids actuate gas flow via the bore 940 to each individual gas nozzle 650 mounted on block 1100. In this manner, the control circuit controls gas flow fed from a gas supply via main supply bore 935 through feeder bores 945 into individual gas supply tubes 930 coupled to the assembly 600.

Figures 12, 13:
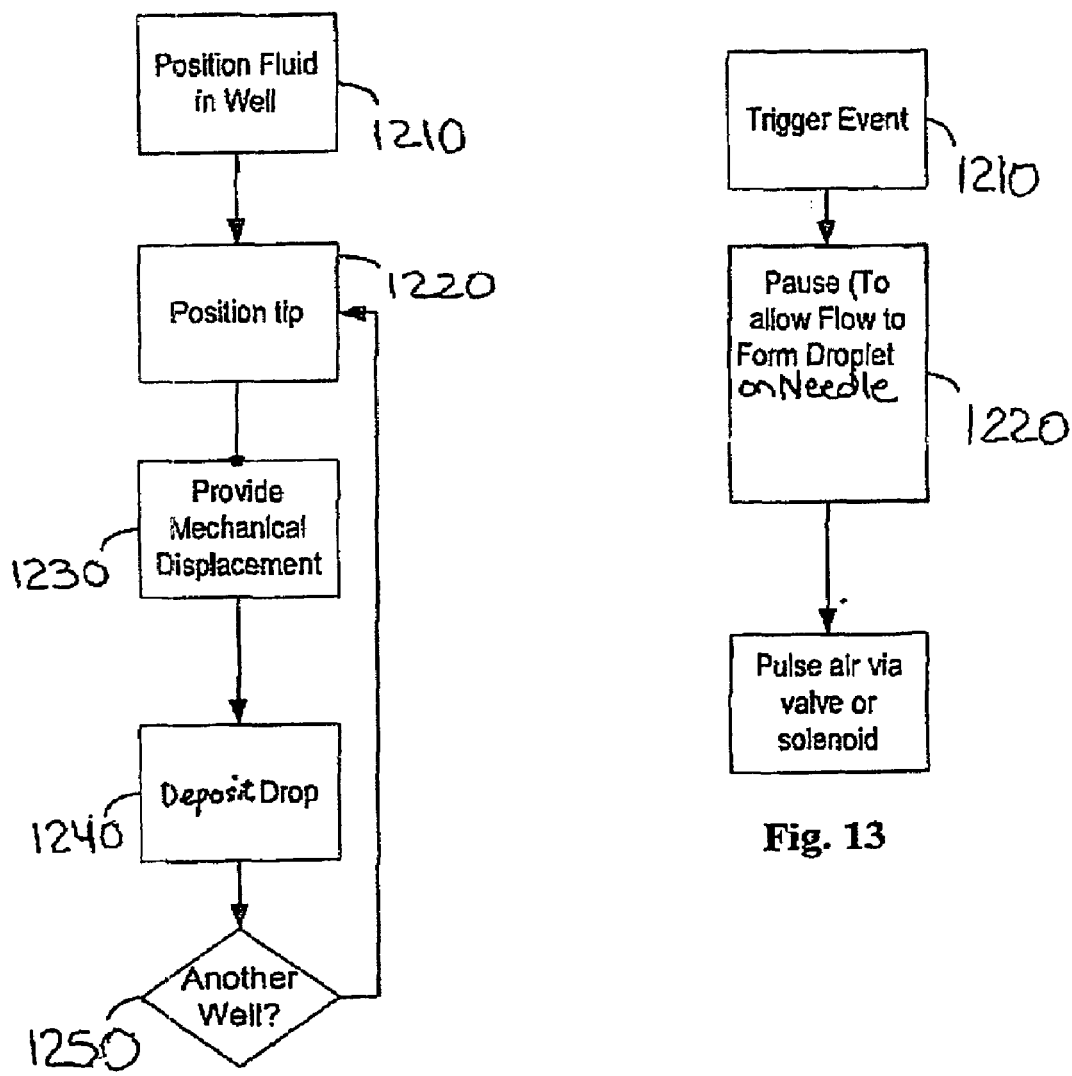
FIG. 12 is a flow chart illustrating a method for utilizing the deposition tip in accordance with the present invention.
FIG. 13 is a flow chart illustrating the timing sequence for actuating a gas flow to the deposition tip of the present invention.

FIG. 12 shows a flow chart illustrating the method for using the system of the present invention. At step 1210, fluid which is desired to be distributed via the system of the present invention is presented in the fluid reservoir 102 shown in FIG. 1. At step 1220, the tip assembly is positioned over the substrate. At step 1230, a mechanical displacement is applied to the fluid causing fluid to traverse the fluid flow path 106 and enter the tip assembly. The pressure of the displacement need only be sufficient to allow fluid to reach the tip. At step 1240, a drop is deposited by actuating the gas flow through the solenoid associated with the tip including the drop and the drop applied. If another well is desired at step 1250, the method returns to step 1220 where the tip is repositioned.

FIG. 13 shows the method for actuating delivery of the drops. In step 1210, some triggering event, such as the provision of mechanical displacement on the fluid, instantiates the method shown in FIG. 13. Following the triggering event, a time lapse is calculated to allow a droplet to form on the tip of the needle. In one embodiment, liquid is displaced from the dispensing head to form a drop at the end of the needle. Next, at step 1230, gas is pulsed to the valve via the needle housing to extract the drop from the needle.

It is noted that ultrasound and other forces, other than gas pressure may be used to effectively push the small volume drop from the needle. For example, in an alternative embodiment, ultrasound actuation is provided to extract the drop from the needle. In this regard, the needle is attached to an ultrasound transducer so that the needle applies a force via ultrasound to drive the small volume drop from the needle.

Figure 14A:
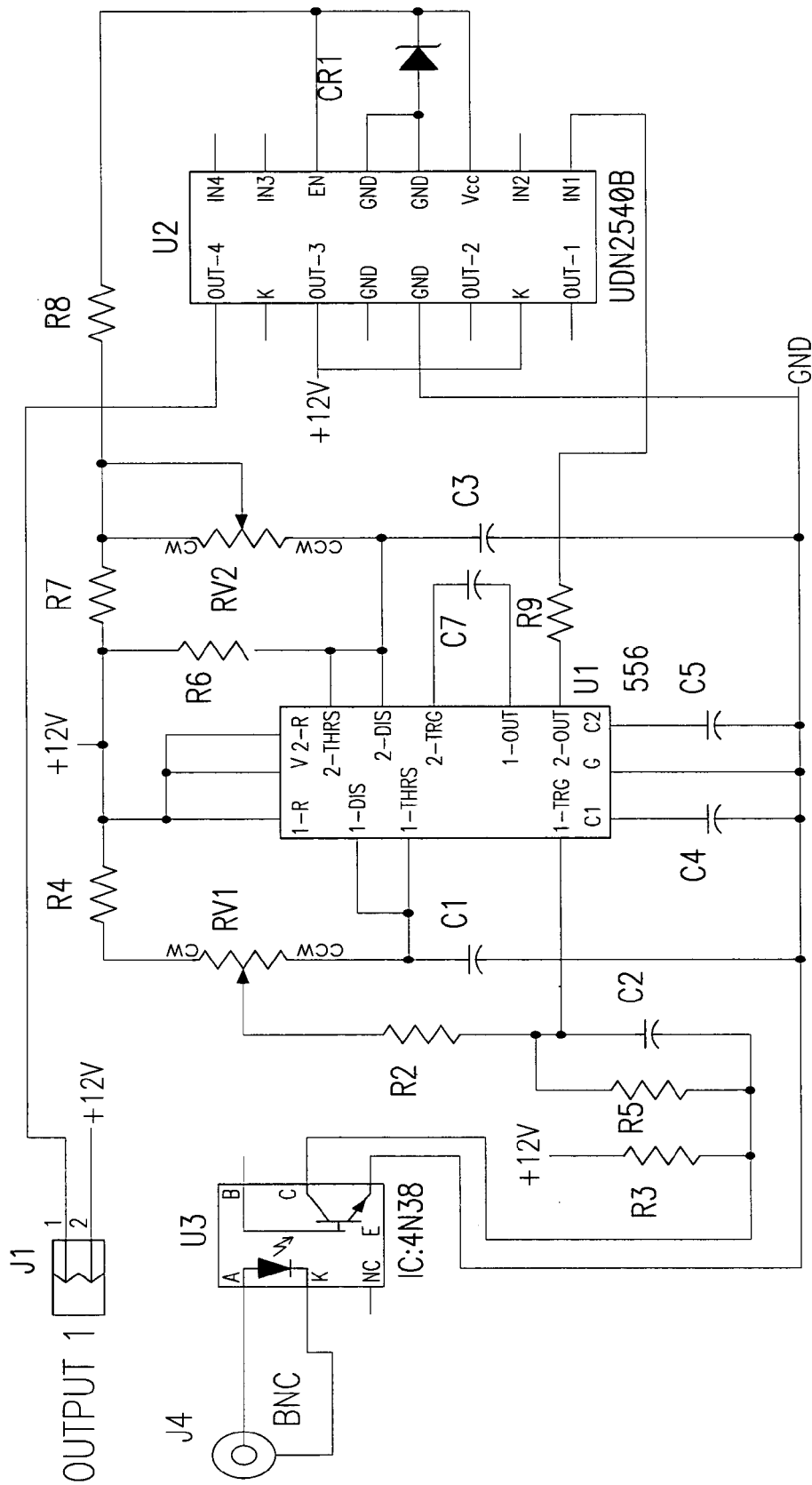
FIG. 14A is a circuit diagram illustrating a timing circuit suitable for actuating a gas pulse to deposit a small volume drop in accordance with the system of the present invention.

FIG. 14A shows one embodiment of a controller suitable for use in the system of the present invention. As illustrated, the controller comprises a timing circuit utilizing well-recognized circuit elements. It should be recognized that the timing can be actuated by software, hardware, or any other suitable control means.

Generally, the circuit of FIG. 14A includes two timers, U1 and U2, each having a triggering input and at least one output. The triggering input is provided via a transistor U3 coupled to a junction J4. The input may be coupled to the event that provides a mechanical displacement to the fluid, and begins the timer sequence shown in FIG. 14B. In general, as noted above, following the triggering event, the circuit pauses for a set amount of time (anywhere from 15 milliseconds to 1 second) to allow for the fluid to move through the tubing network and form a droplet at the end of the needle. The circuit then pulses to open a valve or solenoid that controls the length of time for the gas burst (anywhere from 10 milliseconds to 100 milliseconds).

Figure 14B:
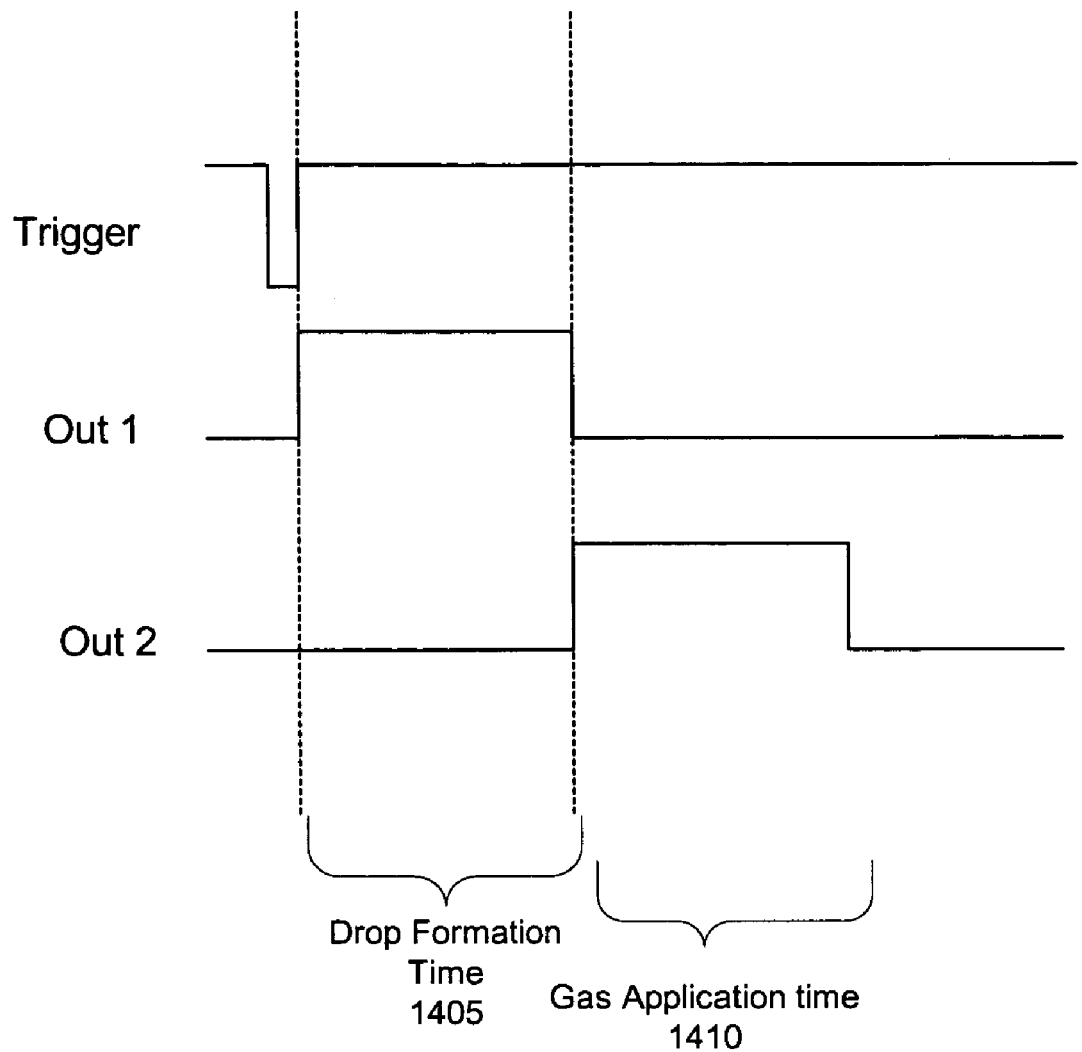
FIG. 14B is a timing diagram illustrating inputs and outputs of the timers in FIG. 14A.

Timer U1 is a conventional 556 timer of the type introduced by Phillips Semiconductor. The 556 timer consists of a pair of 555 timers in one package. The two timers work independently and only share common power supply connections. In FIG. 14A, both timers in U1 are connected in a typical one-shot output arrangement. Integrated circuit U2 may comprise a UDN 2540B Darlington power driver available from any of a number of companies. This device allows an interface between low levels in the processing circuits and power loads on the output, such as the solenoids controlling gas flow to the block 1100. A timing diagram shown in FIG. 14B illustrates the output of timer U1 and power driver U2.

In the basic one-shot mode, timer U1 will be triggered by applying a negative pulse to its trigger input (TRG). This will cause the output of the timer to output a pulse on output 1 as shown in FIG. 13B for a period of time determined by the values of the resistors in the capacitors in the circuits shown in FIG. 14A (essentially RV1 and C1). When the output goes low, output 2 will go high, triggering the input of the power driver U2.

The output of driver U2, shown in FIG. 14A, as provided to junction J1, is provided to a solenoid 1110. As shown in FIG. 14B, the triggering event will cause a first timer to run for a period of time 1405 until triggering the second timer for a period 1410. Time 1405 is the duration necessary to allow formation of the drop under whatever mechanical displacement is used, while time 1410 is the duration of the gas pulse applied by the solenoid. In one embodiment, time 1410 is 50 ms. While the respective times shown in FIG. 14B are relatively equal, it should be realized that any variation of times may be used.

FIGS. 15A-15G illustrate a method for operating the volume delivery station 28 to form hanging drops in each of the wells 38 of a multi-well plate 34. The figures are described with respect to setting up a crystallization experiment for a protein. However, it should be recognized that the same method can be used for setting up other types of crystallization experiments, as well as for setting up crystallization experiments for other types of molecules. It is noted that the station may also be modified for use as a fluid delivery station for other experimental purposes.

Figure 15A:
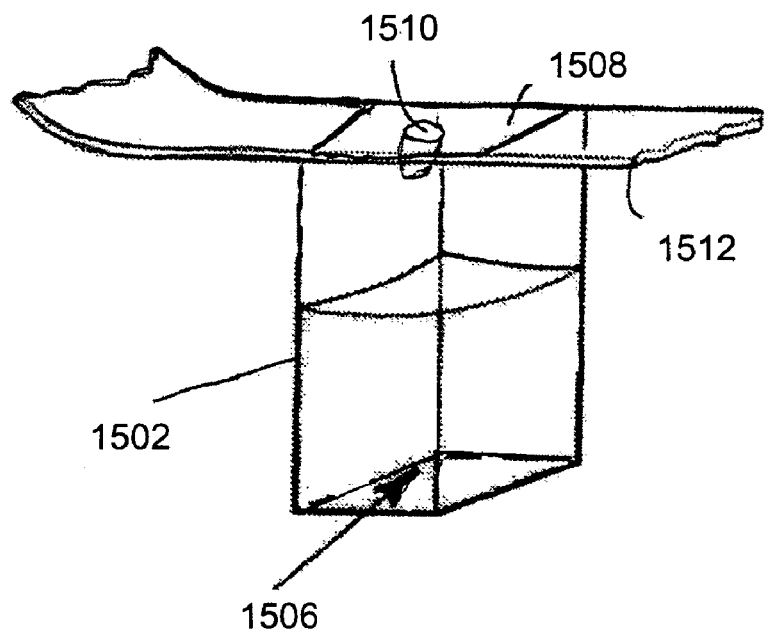
FIGS. 15A through 15G illustrate operation of a volume delivery station designed for hanging drop experiments in multi-well plates.

FIG. 15A illustrates a well of a multi-well plate in which a hanging drop crystallization experiment has been set up. As illustrated, the well 1502 of the multi-well plate comprises a mother liquor solution 1506 which typically varies throughout the wells of the multiwell plate. A cover slip 1508 is positioned over the well 1502 and serves to seal the well. A drop 1510 hangs from a surface of the cover slip opposing the well. Tape 1512 may optionally be used to further seal the well. The drop comprises an aliquot of the mother liquor in the well and an aliquot of a protein solution that comprises the protein being crystallized. As described herein, the drop is typically formed by dispensing the aliquots of mother liquor and protein solution onto the cover slip. The combined volume of these aliquots is typically less than 5 microliters, more typically less than 2 microliters and optionally less than 1 microliter. For example, aliquots having volumes less than 500 nanoliters, 250 nanoliters, 200 nanoliters, 100 nanoliters, 50 nanoliters or less may be dispensed. The precision with which these volumes are delivered is preferably less than about 25 nanoliters per aliquot, more preferably less than 20 nanoliters per aliquot, more preferably less than 15 nanoliters per aliquot, and most preferably less than 10 nanoliters per aliquot.

Figure 15B:
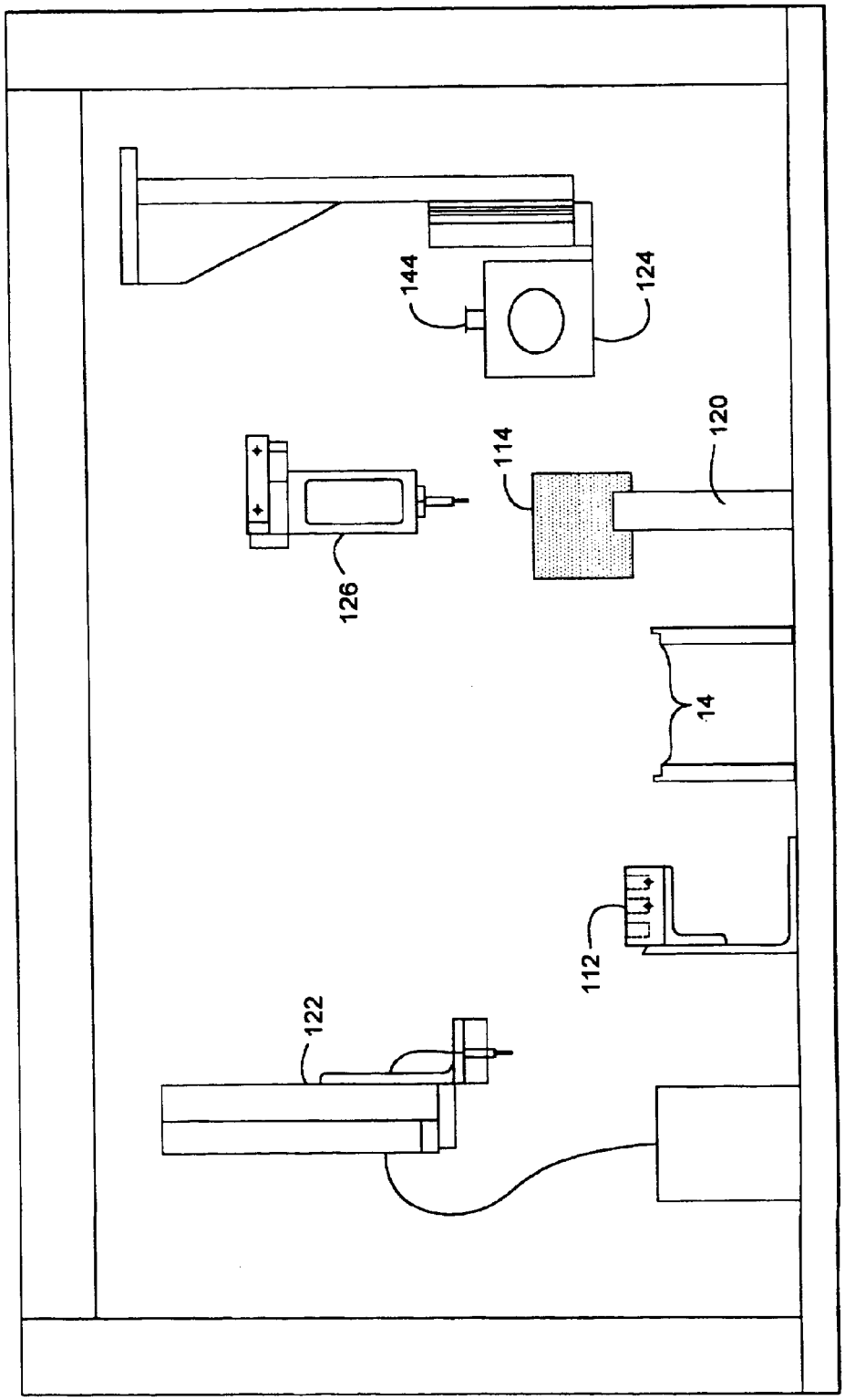

FIG. 15B illustrates a volume delivery station 28 in the rest position which can be occupied when the volume delivery station 28 is not in use or between multi-well plates 34 being transported into the volume delivery station 28. In the rest position, cover slips 144 are attached to the cover slip holder 124 which is positioned to one side of the plate track 14, and the assembly holder 122 is positioned to the opposing side of the plate track 14.

Figure 15C:
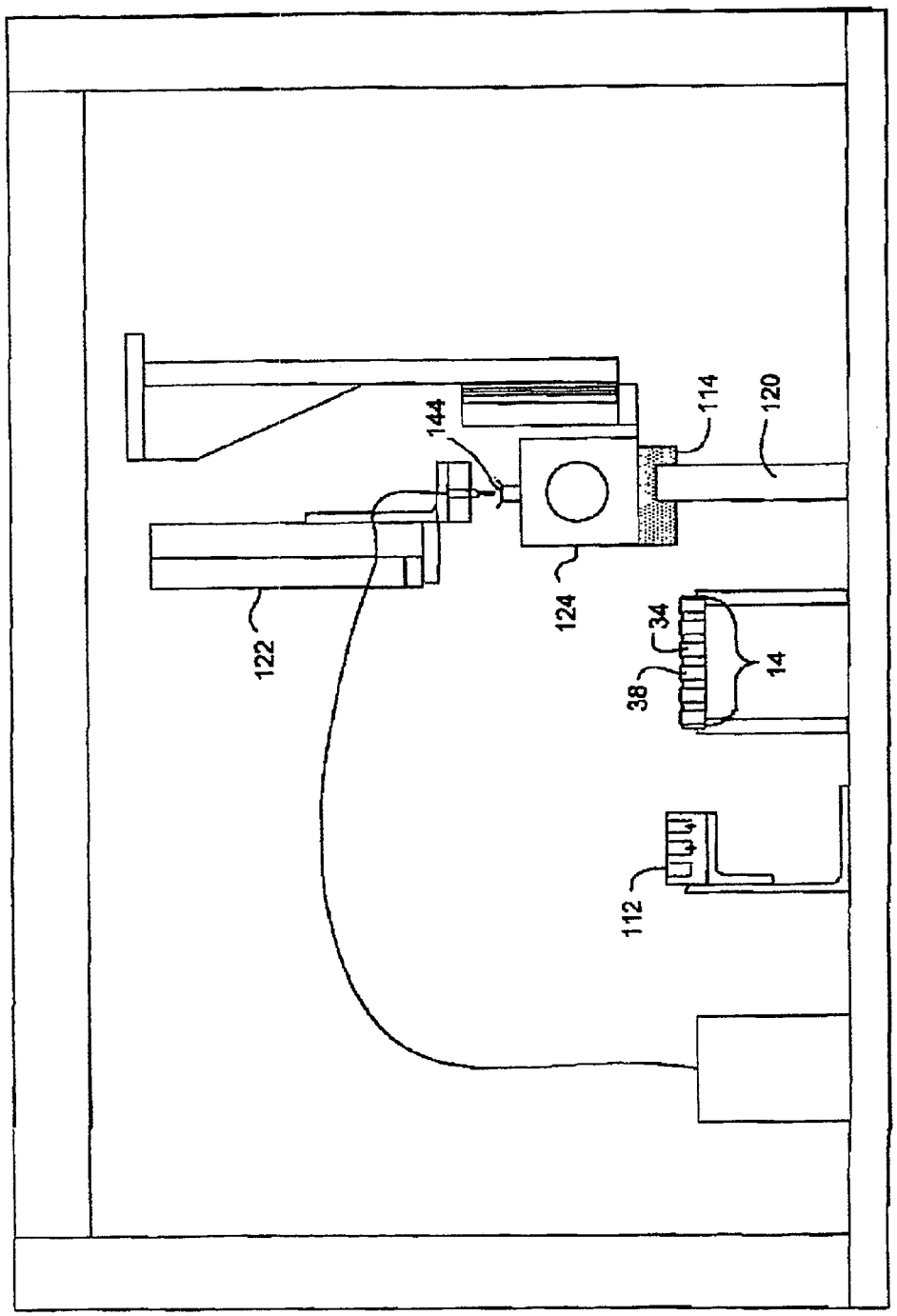

FIG. 15C illustrates the dispensing assembly holder 122 moved over the cover slip holder 124 and positioned so each dispensing assembly tip is aligned with a different support cup 138. The support cups 138 are each holding a cover slip 144 upside down and the attachment mechanism 140 is engaged to immobilize the cover slips 144 relative to the support cups 138. One or more drops of mother liquor are expelled from each dispensing assembly 130 onto the associated cover slips 144. As a result, one or more drops of the mother liquor from a particular well 38 are delivered onto a particular cover slip 144.

The drops of mother liquor are expelled onto the cover slips 144 until a desired volume of mother liquor has been delivered onto each cover slip 144. The total volume of the drops delivered onto the cover slips 144 is strictly controlled. As discussed previously, a feature of the present invention is the ability to deliver small volumes precisely, which enables small drop volumes to be used. The precision of the volumes delivered is preferably less than about 25 nanoliters, more preferably less than 20 nanoliters, more preferably less than 15 nanoliters, and most preferably less than 10 nanoliters.

Figure 15D:
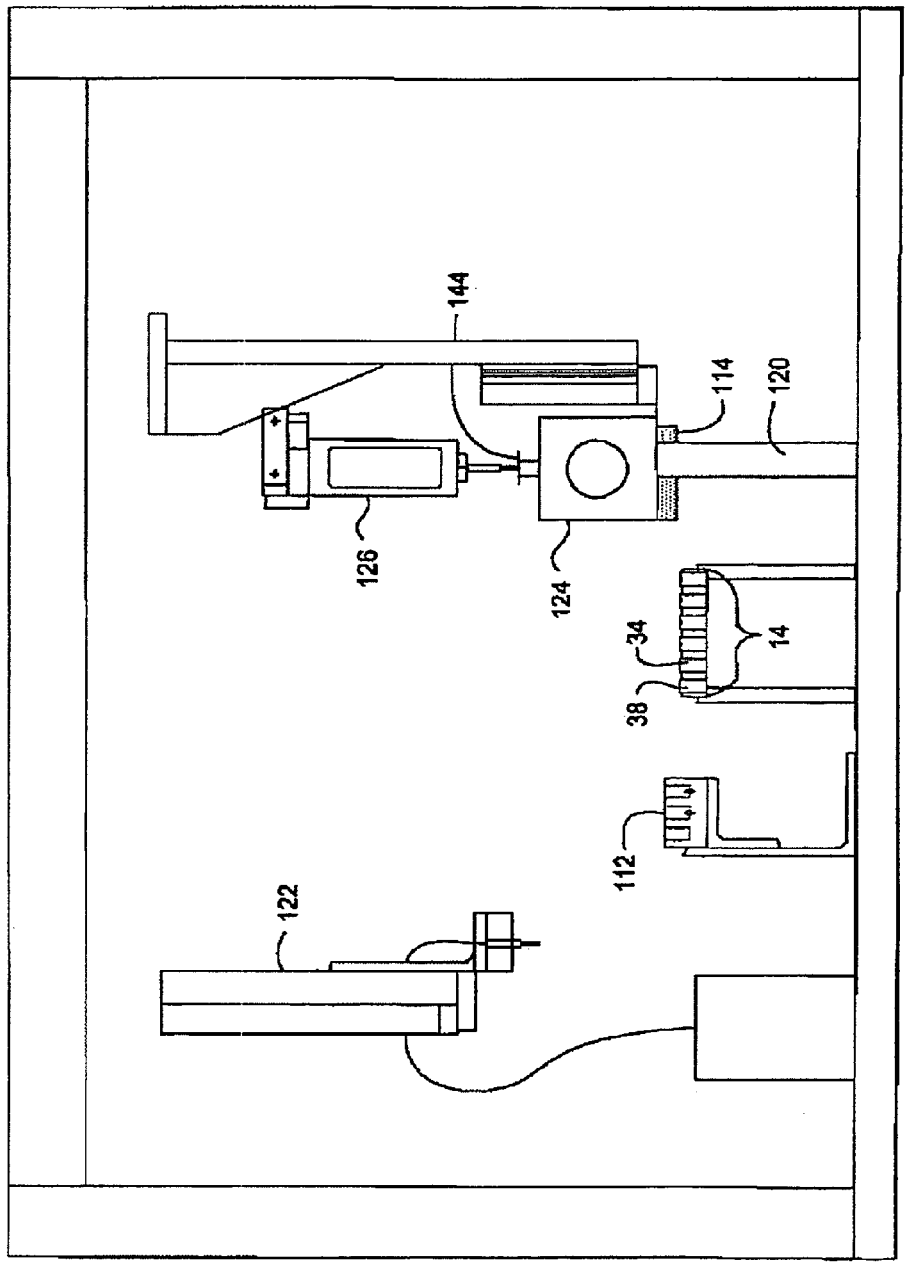

FIG. 15D illustrates the dispensing assembly holder 122 returned to the rest position which was illustrated in FIG. 15B. The molecule delivery pipette 126 is moved into position over a cover slip 144. Before being moved into position over the cover slip 144, the molecule delivery pipette 126 is lowered into a particular molecule solution well and a volume of the molecule solution aspirated. Once the molecule delivery pipette 126 is in position over the cover slip 144, drops of the molecule solution are delivered onto the mother liquor which was previously delivered onto the cover slip 144. The drops of molecule solution are delivered until a desired volume of molecule solution is achieved on the cover slip 144. The precision of the volumes delivered is preferably less than about 25 nanoliters, more preferably less than 20 nanoliters, more preferably less than 15 nanoliters, and most preferably less than 10 nanoliters.

The mother liquor drops and the protein drops may be delivered in any order. Once both drops are delivered, the drops combine to form a hanging drop to be studied for crystal formation.

After forming a hanging drop on the cover slip 144, the molecule delivery pipette 126 proceeds to the next cover slip 144 until a hanging drop is formed on each cover slip 144. The molecule delivery pipette 126 then returns to the position over the molecule solution well which was the source for the molecule solution used to create the hanging drops. The molecule solution remaining in the molecule delivery pipette 126 is expelled into the molecule solution well.

Figure 15E:
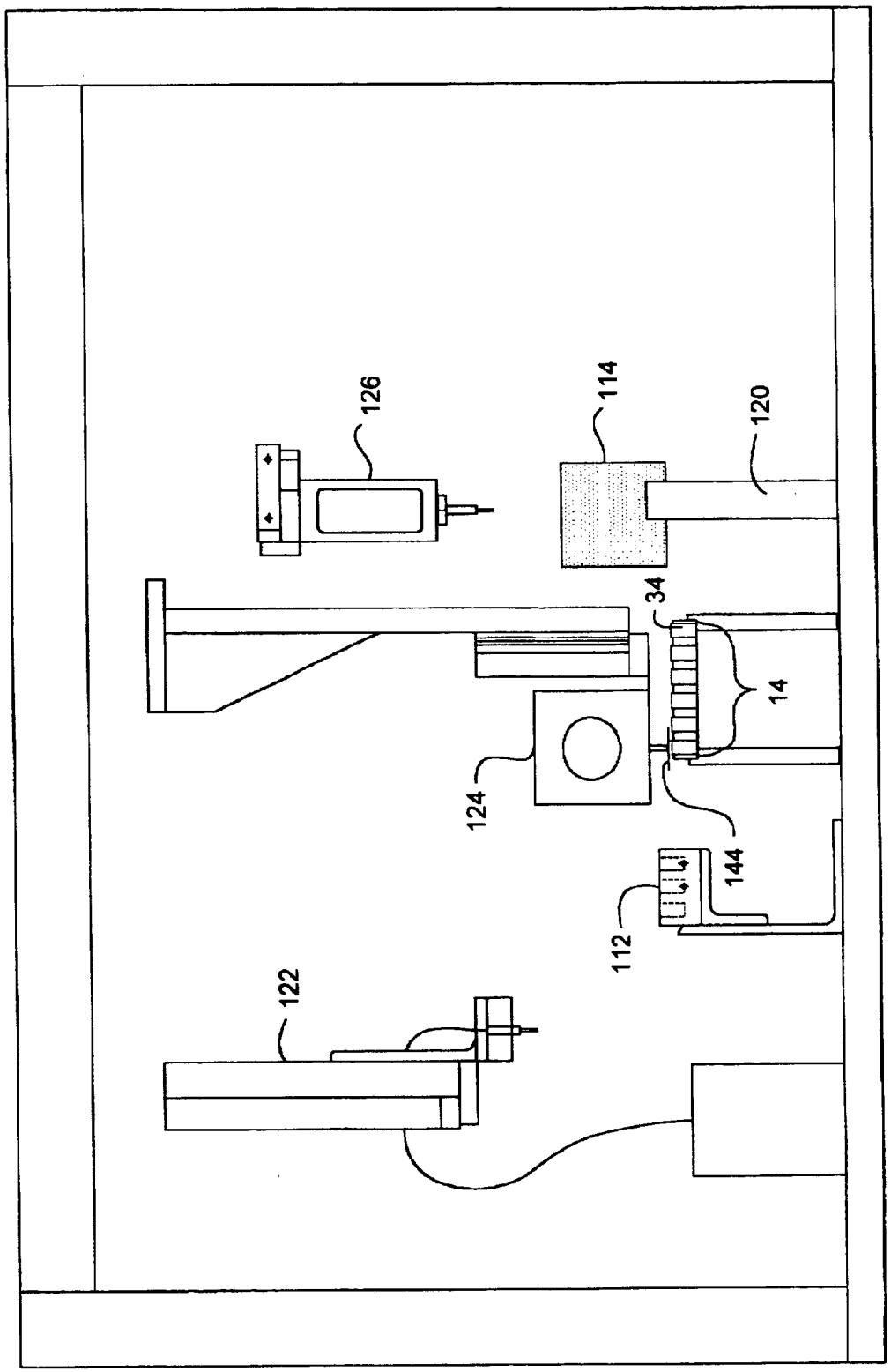

FIG. 15E illustrates the molecule delivery pipette 126 returned to its rest position as illustrated in FIG. 15A. FIG. 15E also illustrates the cover slip holder 124 inverted and moved into position over the column of wells 38 on the multi-well plate 34. The cover slip holder 124 is positioned so each cover slip 144 is aligned with a different well 38 in the column. Specifically, a given cover slip 144 is aligned with the well 38 which was the source of the mother liquor used to create the hanging drop on the given well 38.

Figure 15F:
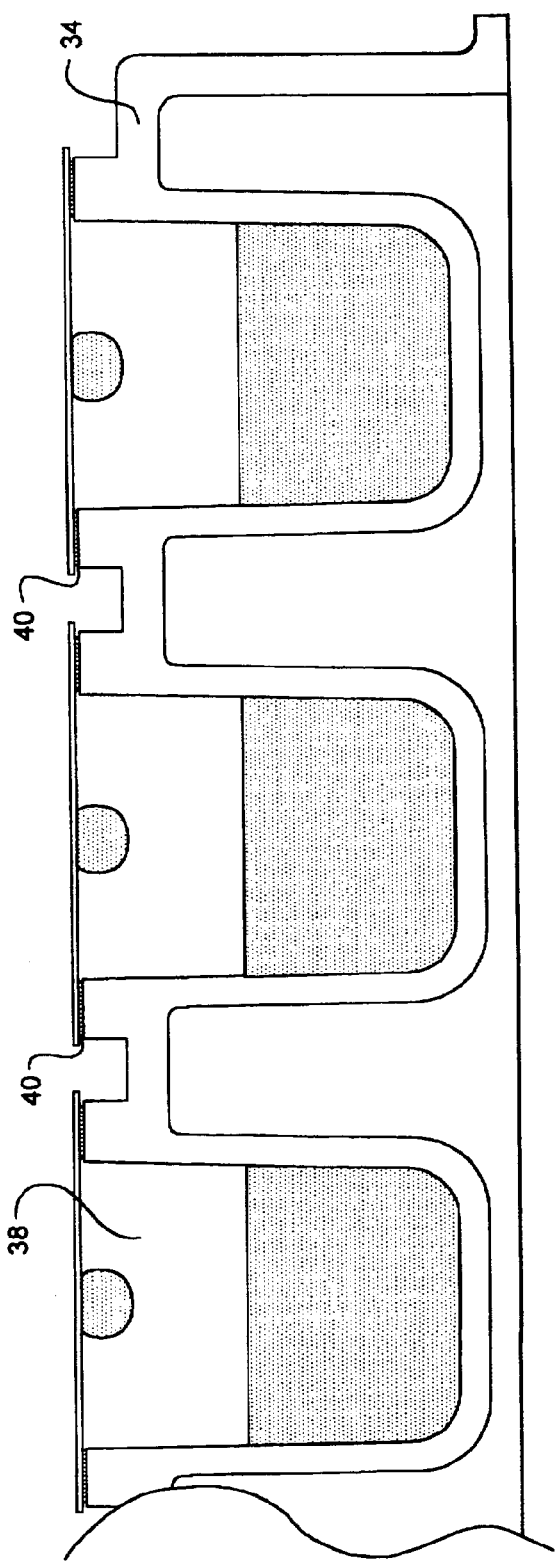

The cover slip holder 124 is lowered until the cover slips 144 contact the upper edges 40 of the associated wells 38. The sealing medium which was previously applied to the upper edge 40 of the wells 38 causes a seal to be formed between the cover slips 144 and the upper edges 40 of the associated wells 38. The attachment mechanism 140 is released and the cover slip holder 124 is raised to leave each cover slip 144 in place over an associated well 38. The hanging drop hangs from the cover slips 144 into the wells 38 as illustrated in FIG. 15F.

Figure 15G:
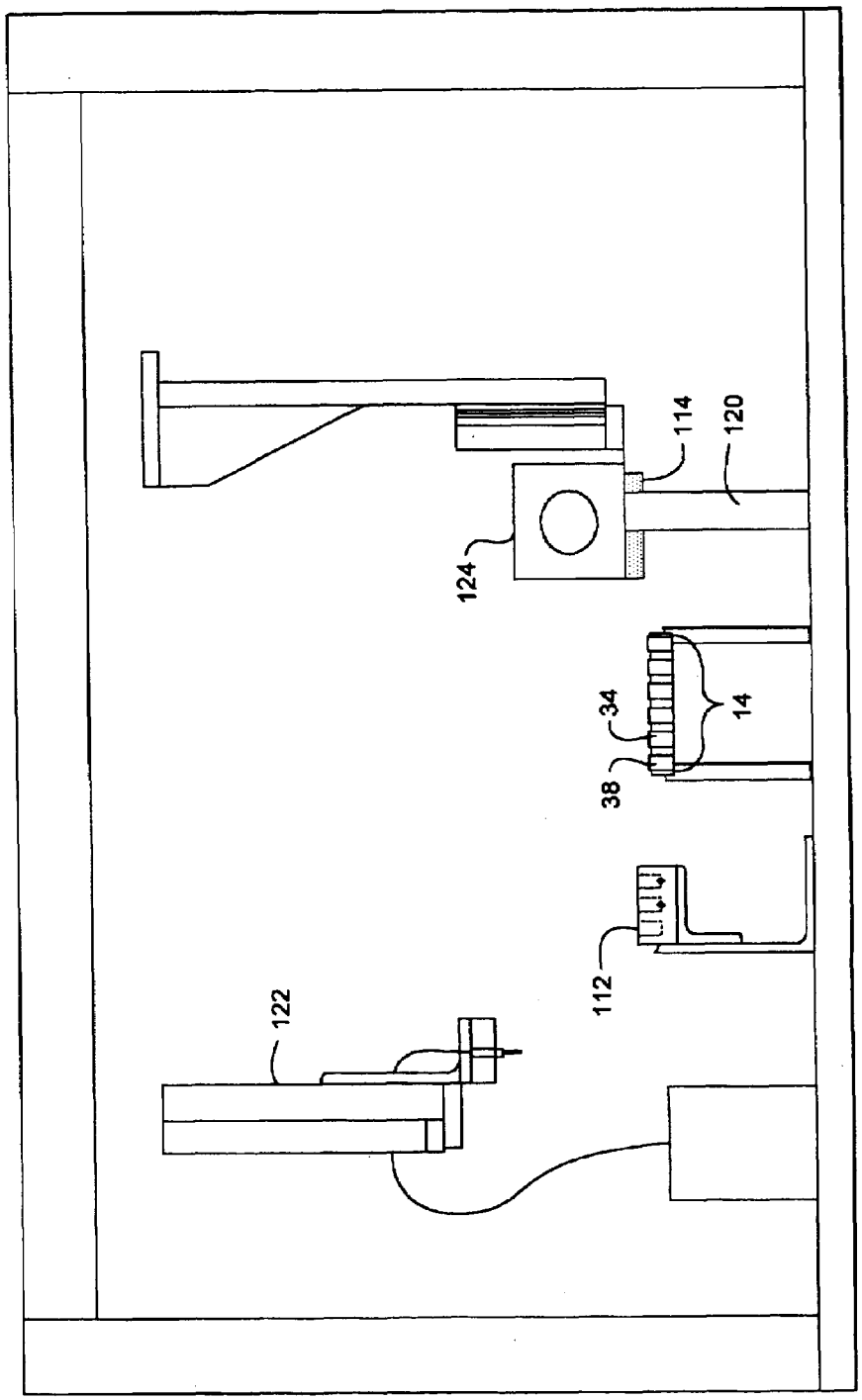

FIG. 15G illustrates the cover slip holder 124 moved into position over the cover slip storage component 120. The cover slip holder 124 is positioned so each support cup 138 is aligned with a magazine 142 in the cover slip storage component 120. Accordingly, each support cup 138 is associated with the top cover slip 144 in each magazine 142. The cover slip holder 124 is lowered until each support cup 138 contacts a cover slip 144 within the associated magazine 142. The attachment mechanism 140 is engaged to immobilize the contacted cover slips 144 relative to the associated support cups 138.

FIG. 15G illustrates the cover slip holder 124 returned to its rest position. The top cover slip 144 from each magazine 142 discussed with respect to FIG. 15F is attached to the associated support cup 138.

The steps described with respect to FIGS. 15B-15G result in a hanging drop being formed in each well 38 of a single column of wells 38. These steps are repeated until a hanging drop is formed in the wells 38 of each column of the multi-well plate 34. Once a hanging drop is formed in each of the wells 38, the multi-well plate 34 can be moved to the next station.

Figure 16A:
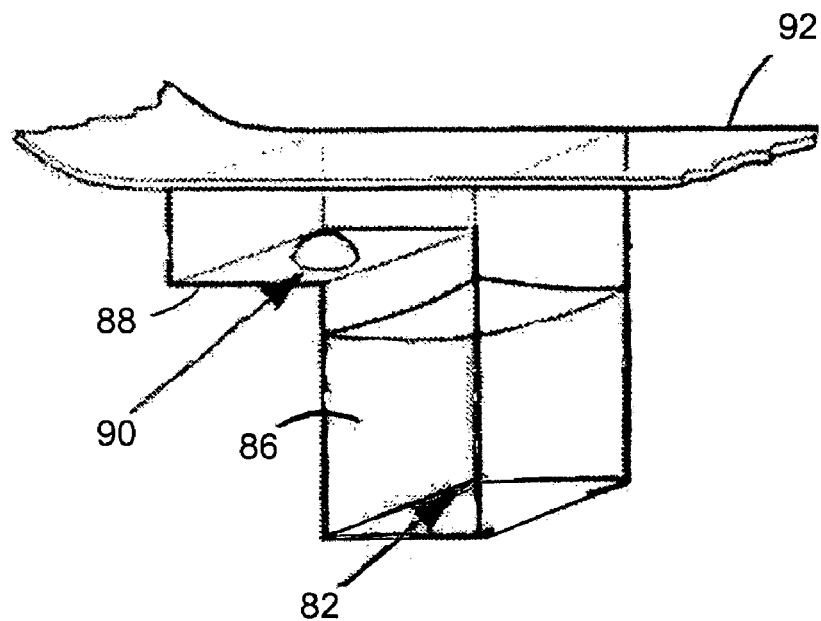
FIGS. 16A through 16F illustrate operation of the volume delivery station to form sitting drops.

FIG. 16A illustrates a well of a multi-well plate in which a sitting drop crystallization experiment has been set up. As illustrated, the well 82 of the multi-well plate comprises a mother liquor solution 86 which typically varies throughout the wells of the multiwell plate. A drop 90 sits on a shelf 88 adjacent the well 82. Tape 92 is used to seal the well 82. The drop comprises an aliquot of the mother liquor in the well and an aliquot of a protein solution that comprises to the protein being crystallized. As described herein, the drop is typically formed by dispensing the aliquots of mother liquor and protein solution onto the shelf 88. The combined volumes of these aliquots is typically less than 5 microliters, more typically less than 2 microliters and optionally less than 1 microliter. For example, aliquots having volumes less than 500 nanoliters, 250 nanoliters, 200 nanoliters, 100 nanoliters, 50 nanoliters or less may be dispensed. The precision with which these volumes are delivered is preferably less than about 25 nanoliters per aliquot, more preferably less than 20 nanoliters per aliquot, more preferably less than 15 nanoliters per aliquot, and most preferably less than 10 nanoliters per aliquot.

As can be seen, sitting drop crystallization experiments have a similar but different arrangement than hanging drop crystallization experiments.

The system described in FIGS. 15B-15G can be readily adapted to form sitting drops. This adaptation can be made with changes to the mother liquor delivery station and the volume delivery station 28. For instance, the mother liquor delivery station may be adapted to deliver mother liquor into the well regions 41 of a multi-well plate 34 adapted to perform a sitting drop array crystallizations. Specifically, the fluid injectors of the mother liquor delivery station must be aligned with the well regions 41 before the mother liquor is delivered into the wells 38 of the multi-well plate 34. This alignment permits delivery of the mother liquor into the well region 41 of each well 38 without delivering the mother liquor onto the sitting drop region 42 of each well 38.

FIGS. 16B-16F illustrate a method for operating the volume delivery station 28 to form sitting drops in each well 38 of a multi-well plate 34.

Figure 16B:
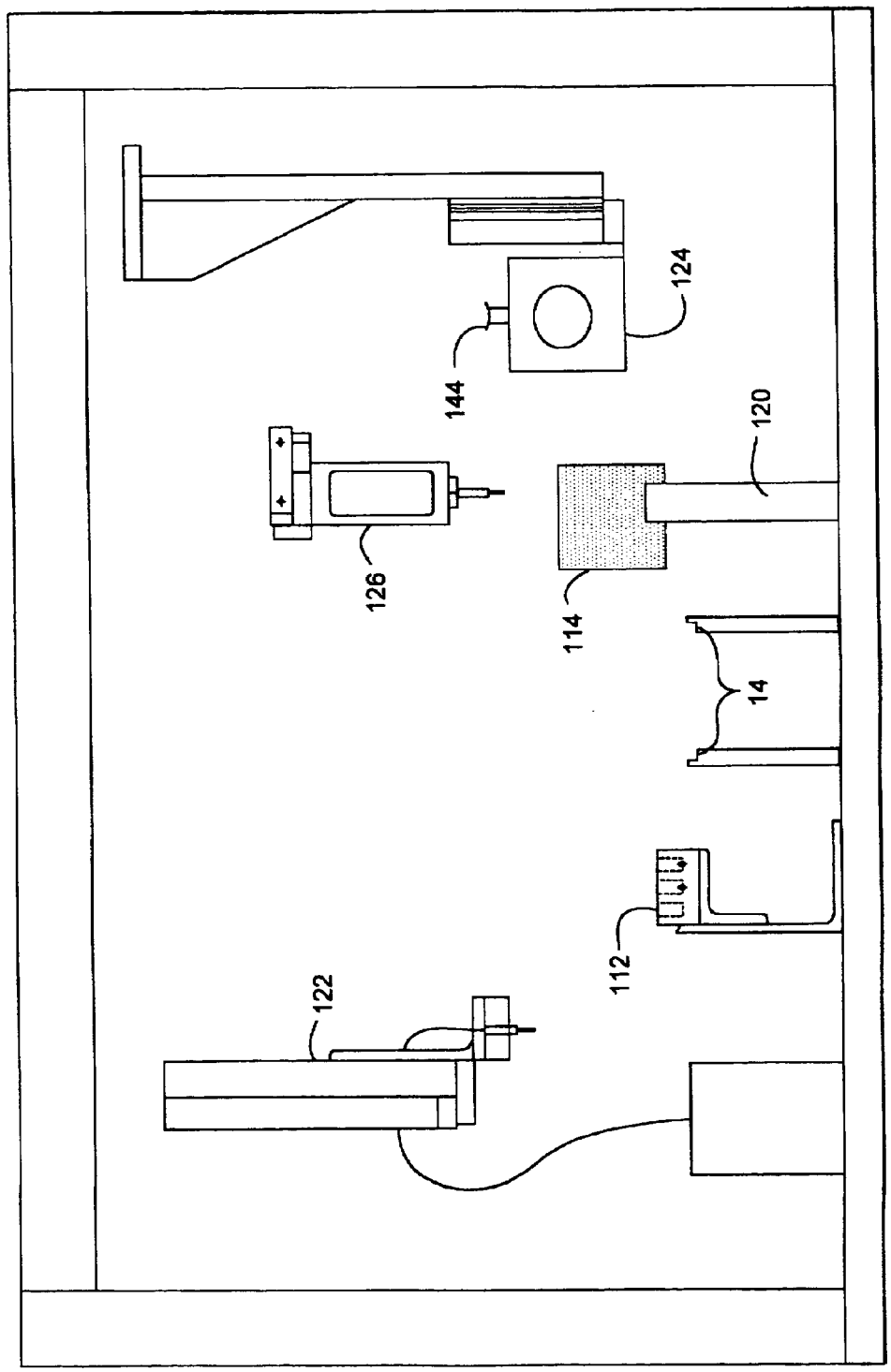
Figure 16C:
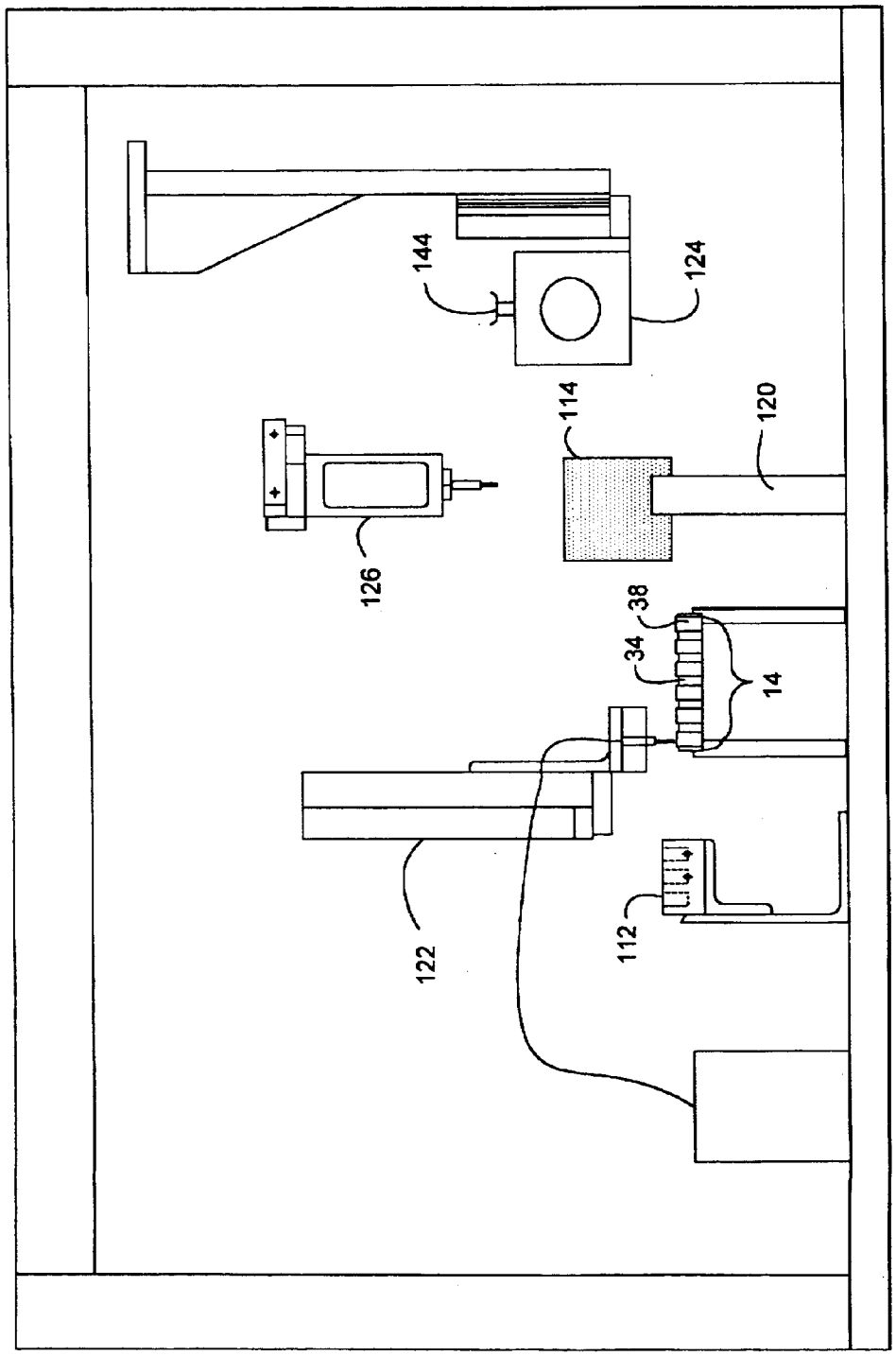

The figures are described with respect to crystallization of a protein, however, the same method can be used for crystallization of other types of molecules. FIG. 16B illustrates the volume delivery station 28 in the same rest position illustrated in FIG. 15B. FIG. 16C illustrates a multi-well plate 34 adapted to perform a sitting drop array micro crystallization moved into position for sitting volume delivery. Accordingly, each well 38 in the multi-well plate 34 includes a well region 41 adjacent to a sitting drop region 42.

Figure 16D:
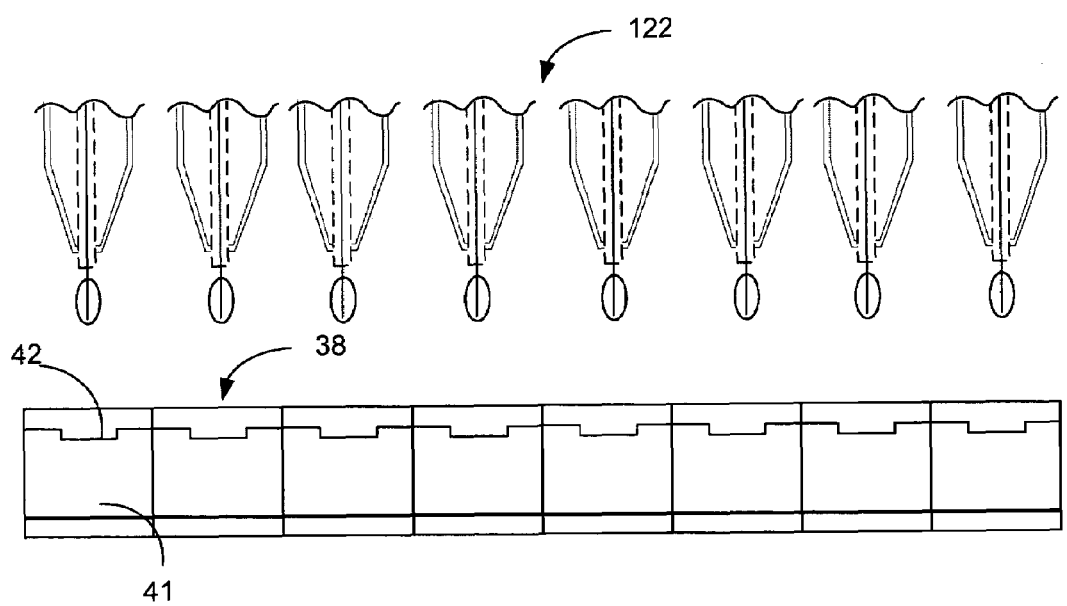

FIG. 16D illustrates the assembly holder 122 moved into position over a column of wells 38 in the multi-well plate 34.

The deposition assembly holder 122 is then moved so each assembly tip is aligned with the region 41 in a different well 38 in the column as illustrated in FIG. 16D. One or more drops of mother liquor is expelled from each assembly onto the associated region 41. As a result, one or more drops of the mother liquor are delivered to a particular well region 41. The drops of mother liquor are expelled onto the region 41 until a desired volume of mother liquor has been delivered onto each region 41. Proteins are then delivered to drop region 42. It should be understood that in an alternative embodiment, the more liquor may be delivered to region 42 along with the protein.

Figure 16F:
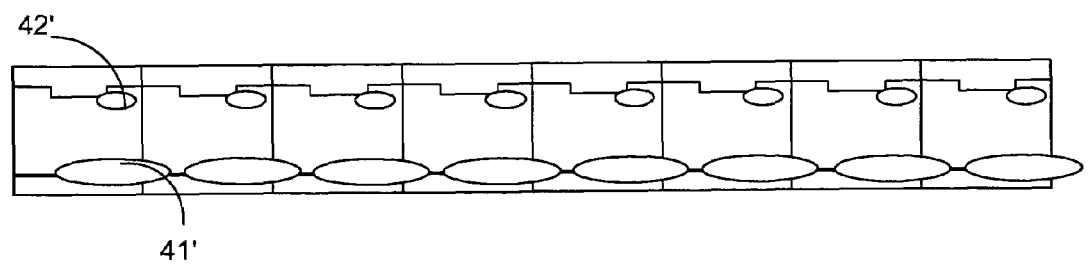
Figure 16E:
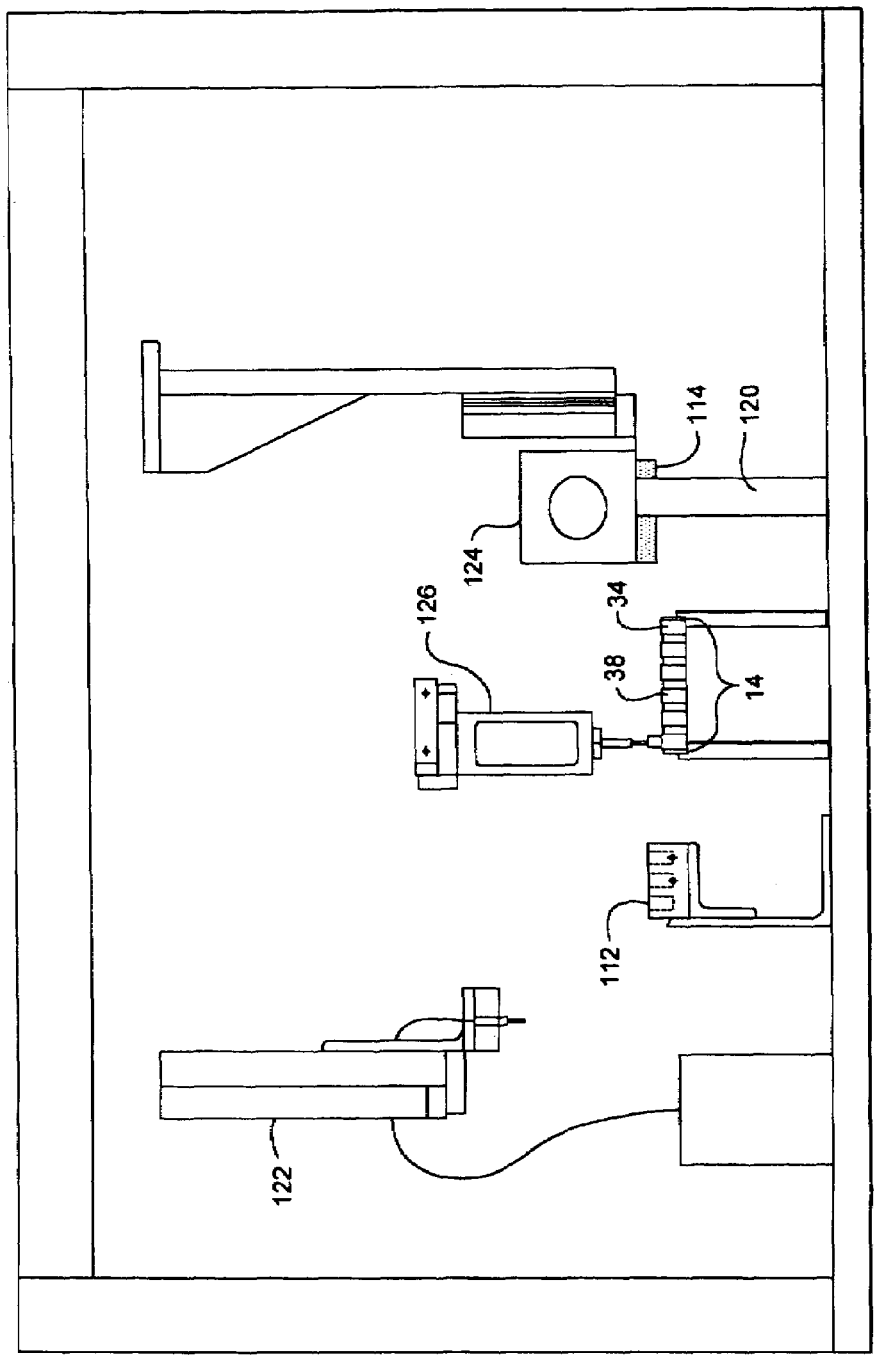

FIG. 16E illustrates the dispensing assembly holder 122 returned to the rest position which was illustrated in FIG. 16B. The molecule delivery pipette 126 is moved into position over a sitting drop region 42 in a well 38 of the column. Before being moved into position over the well 38, the molecule delivery pipette 126 was lowered into a particular molecule solution well and a volume of the molecule solution aspirated. Once the molecule delivery pipette 126 is in position over the sitting drop region 42, drops of the molecule solution are delivered onto the region 42. The drops of molecule solution are delivered until a desired volume of molecule solution is achieved on the sitting drop region 42. The precision of the volumes delivered is preferably less than about 25 nanoliters, more preferably less than 20 nanoliters, more preferably less than 15 nanoliters, and most preferably less than 10 nanoliters.

The mother liquor drops and the protein drops may be delivered in any order. Once both drops are delivered, the drops combine to form a sitting drop to be studied for crystal formation. FIG. 16F illustrates sitting drops 42' and mother liquor drops 41' formed on the sitting drop region 42 of a well 38. After forming the sitting drop on the sitting drop region 42, the molecule delivery pipette 126 proceeds to the sitting drop region 42 in the next well 38 until a sitting drop is formed in each well 38 of the column. The molecule delivery pipette 126 then returns to the position over the molecule solution well which was the source for the molecule solution used to create the sitting drops. The molecule solution remaining in the molecule delivery pipette 126 is expelled into the molecule solution well.

The steps described with respect to FIGS. 16B-16F result in a sitting drop being formed in each well 38 of a single column of wells. These steps are repeated until a drop is formed in the wells 38 of each column of the multi-well plate 34. Once a hanging drop is formed in each of the wells 38, the multi-well plate 34 can be moved to the next station.

Figure 17A:
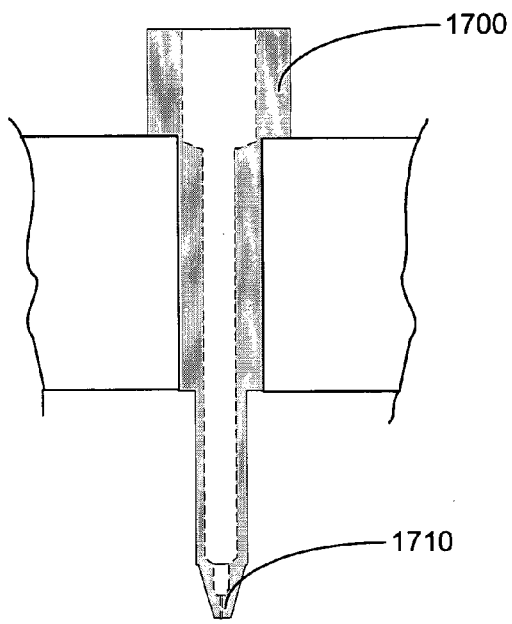
FIG. 17A illustrates a prior art pipette utilized to provide small volume drops in commercial liquid handling apparatus.
Figure 17B:
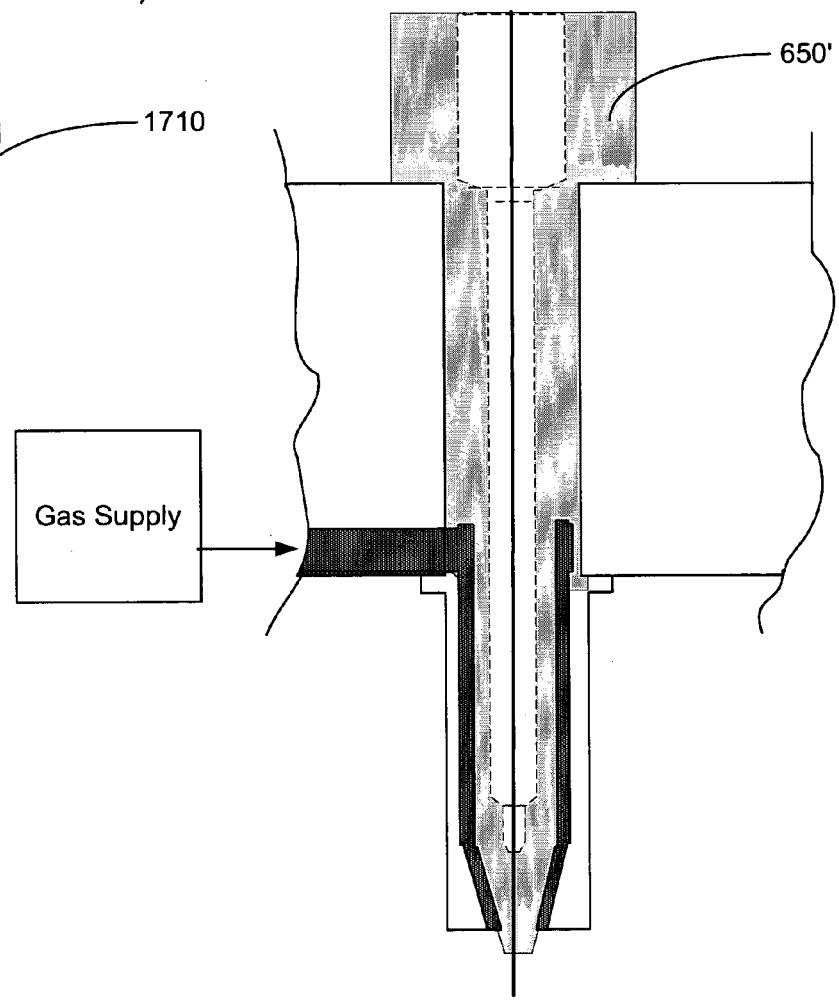
FIG. 17B illustrates a retrofit dispensing system adapted to be used with commercial liquid handling apparatus.

FIGS. 17A and 17B show yet another embodiment of the present invention wherein the principles of the present invention are applied to standard commercial liquid handling devices and applied in a retrofit fashion to enable these devices to be utilized in accordance with the principles of the present invention. FIG. 17A shows a standard pipette 1700 and deposition tip 1710 utilized in any number of commercial liquid handling devices. Such devices are available from the companies described above, including Beckman Colter Corporation, Zymark Corporation, Packard Bioscience, and Gilson Corporation, including the 215 liquid handler work station. As shown in FIG. 17A, the original pipette includes a central bore tapering to a thin deposition tip. FIG. 17B shows the retrofit assembly 650' which provides a simple hardware addition to existing technology by adding an insert to the existing orifice. This assembly reduces the liquid surface contact area from the liquid fluid in the system to the outside fluid that will form the drop on the needle. A retrofit gas pressure assembly and solenoid feed the dispensing assembly 650'. A droplet is guided down the needle and into the desired receptacle when the gas solenoid is actuated and imparts a force on the droplet that overcomes surface tension and viscous bonds.

The systems described above are industry standard robot liquid handling systems that automate many kinds of lab procedures. Many of the tips are attached to an XYZ motor and controlled by software that allows a user to move the tips around a deck that has any possible variance of labware, including 96-well, 384-well, and 1536-well microliter plates, tubes, vials, glass lights, reservoirs, etc. A software interface allows freedom to move from one piece of equipment and aspirate and dispense volumes of amounts of fluid from one area to another in order to complete a procedure.

By retrofitting commercial instruments with a gas dispense system according to the present invention, the performance of these instruments can be greatly improved. For example, by improving the effectiveness with which small volumes separate from tips, the volumes that these instruments can dispense can be reduced significantly, in sum instances by a factor greater than 5× or 10×. In addition to the resolution increase, the systems are able to dispense volumes without contact "touch-off", thereby eliminating many of the difficulties associated with having to actually contact the substrate in order to dispense fluid. By greatly improving the performance of existing instruments in these regards, the instruments may be used for a variety of functions for which they are not now currently used. For example, the instruments can be used to scale down experiment and reaction volumes significantly, thus allowing denser arrays to be formed and/or allowing less material to be used. Further, by allowing the instruments to operate contact free, the instruments are able to deliver more volumes per unit time.

Despite the specific exemplifications provided, it should be recognized that many variations to the system of the present invention are possible and are intended to be within the scope of the overall invention. For example, the gas nozzle and gas dispensing system may optionally be replaced with an ultrasound wave generator coupled to the needle, the pipette or both. Instead of actuating the gas flow about the drop on the needle, an ultrasonic pulse of sufficient duration and energy can be applied to the assembly to dislodge the drop from the needle.

The foregoing detailed description of the invention has been presented for purposes of illustration and description. It is not intended to be exhaustive or to limit the invention to the precise form disclosed. Many modifications and variations are possible in light of the above teaching. For example, piezoelectric, micromechanical, or other droplet break-off mechanisms can be utilized in accordance with the principles of the present invention, and the assembly shown herein. The described embodiments were chosen in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. A fluid dispensing system comprising:
   a fluid container;
   a dispensing head in fluid communication with the fluid container;
   a displacement mechanism which delivers fluid from the fluid container to the dispensing head such that an aliquot of liquid is delivered to a distal end of the dispensing head where the aliquot of liquid is retained due to surface tension between the liquid and the distal end of the dispensing head; and
   a pressurized gas displacement mechanism which delivers an aliquot of gas to the distal end of the dispensing head which causes the aliquot of liquid retained at the distal end of the dispensing head to separate from the distal end of the dispensing head;
   wherein the dispensing head defines a lumen through which the aliquot of liquid is delivered to the distal end of the dispensing head and a needle positioned within the lumen that extends beyond the distal end of the lumen, the needle forming the distal end of the dispensing head where the aliquot of liquid is retained.

2. A fluid dispensing system according to claim 1 wherein the displacement mechanism is a mechanical displacement mechanism.

3. A fluid dispensing system according to claim 1 wherein the displacement mechanism is selected from the group consisting of a syringe, a pump, an electrophoretic device and a mechanical displacement device.

4. A fluid dispensing system according to claim 1 wherein the pressurized gas displacement mechanism delivers the aliquot of gas to the aliquot of liquid to cause the aliquot of liquid to separate from the distal end of the dispensing head.

5. A fluid dispensing system according to claim 1 wherein the dispensing head defines a lumen through which the aliquot of liquid is delivered to the distal end of the dispensing head.

6. A fluid dispensing system according to claim 1 wherein the dispensing head defines a lumen through which the aliquot of liquid is delivered to the distal end of the dispensing head and a gas housing through which the aliquot of gas is delivered to the distal end of the dispensing head.

7. A fluid dispensing system according to claim 6 wherein the lumen is surrounded by an outer gas housing through which the aliquot of gas is delivered to the distal end of the dispensing head.

8. A fluid dispensing system according to claim 1 wherein the dispensing head further defines a gas housing through which the aliquot of gas is delivered to the distal end of the dispensing head.

9. A fluid dispensing system according to claim 1 wherein the aliquot of liquid dispensed has a volume of less than 1 microliter.

10. A fluid dispensing system according to claim 1 wherein the pressurized gas displacement mechanism controls the energy supplied by the aliquot of gas within a range of 0.001 W to 100 W.

11. A fluid dispensing system according to claim 1 wherein the pressurized gas displacement mechanism controls the weight of the aliquot of gas released within a range of $10^{-10}$ to about $10^{-4}$ kg.

12. A fluid dispensing system according to claim 1 wherein the pressurized gas displacement mechanism controls the pressure of the aliquot of gas released within a range of 0.05 psi to 50 psi.

13. A fluid dispensing system according to claim 1 wherein the pressurized gas displacement mechanism causes the aliquot of liquid to be dispensed without aerating the aliquot of liquid.

14. A fluid dispensing system according to claim 1 wherein the fluid dispensing system further comprises a pressurized gas source regulated by a flow valve to the dispensing head.

15. A fluid dispensing system according to claim 14 wherein the fluid dispensing system further comprises a controller that actuates the flow valve to release a discontinuous aliquot of gas.

16. A fluid dispensing system according to claim 1 wherein the fluid dispensing system further includes a controller coupled to actuate a gas supply coupled to the pressurized gas displacement mechanism.

17. A fluid dispensing system according to claim 1 wherein the pressurized gas displacement mechanism comprises a solenoid valve.

18. A fluid dispensing system according to claim 1 wherein the fluid dispensing system further includes a controller coupled to actuate a solenoid valve of the pressurized gas displacement mechanism.

19. A fluid dispensing system according to claim 1 wherein the fluid dispensing system further includes a controller comprising a timer circuit which times operation of the pressurized gas displacement mechanism relative to operation of the displacement mechanism.

20. A fluid dispensing system according to claim 1 wherein the fluid dispensing system further includes a controller comprising a timer circuit which operates the pressurized gas displacement mechanism to release an aliquot of gas after operation of the displacement mechanism.

21. A fluid dispensing system according to claim 1 wherein the fluid dispensing system comprises a plurality of dispensing heads mounted to a mounting block which comprises gas supply bores for supplying gas to each of the plurality of dispensing heads.

22. A fluid dispensing system according to claim 1 wherein the fluid dispensing system comprises at least one gas control solenoid coupled between the displacement mechanism and the pressurized gas displacement mechanism.

23. A fluid dispenser head comprising: a dispensing head through which an aliquot of liquid is delivered to a distal end of the dispensing head where the aliquot of liquid is retained due to surface tension between the liquid and the distal end of the dispensing head; and a pressurized gas displacement mechanism which delivers an aliquot of gas to the distal end of the dispensing head which causes the aliquot of liquid retained at the distal end of the dispensing head to separate from the distal end of the dispensing head, wherein the dispensing head defines a lumen through which the aliquot of liquid is delivered to the distal end of the dispensing head and a needle positioned within the lumen that extends beyond the distal end of the lumen, the needle forming the distal end of the dispensing head where the aliquot of liquid is retained.

24. A fluid dispenser head according to claim 23 wherein the dispensing head defines a lumen through which the aliquot of liquid is delivered to the distal end of the dispensing head.

25. A fluid dispenser head according to claim 24 wherein the lumen is surrounded by an outer gas housing through which the aliquot of gas is delivered to the distal end of the dispensing head.

26. A fluid dispenser head according to claim 23 wherein the dispensing head defines a lumen through which the aliquot of liquid is delivered to the distal end of the dispensing head and a gas housing through which the aliquot of gas is delivered to the distal end of the dispensing head.

27. A fluid dispenser head according to claim 23 wherein the dispensing head further defines a gas housing through which the aliquot of gas is delivered to the distal end of the dispensing head.

28. A fluid dispenser head according to claim 23 wherein the aliquot of liquid dispensed has a volume of less than 1 microliter.

29. A fluid dispenser head according to claim 23 wherein the pressurized gas displacement mechanism controls the energy supplied by the aliquot of gas within a range of 0.001 W to 100 W.

30. A fluid dispenser head according to claim 23 wherein the pressurized gas displacement mechanism controls the weight of the aliquot of gas released within a range of $10^{-10}$ to about $10^{-4}$ kg.

31. A fluid dispenser head according to claim 23 wherein the pressurized gas displacement mechanism controls the pressure of the aliquot of gas released within a range of 0.05 psi to 50 psi.

32. A fluid dispenser head according to claim 23 wherein the pressurized gas displacement mechanism causes the aliquot of liquid to be dispensed without aerating the aliquot of liquid.

* * * * *